(12) United States Patent
Thurston

(10) Patent No.: US 6,191,422 B1
(45) Date of Patent: Feb. 20, 2001

(54) RADIATION PROBE WITH COMPOUND SEMICONDUCTOR CRYSTAL PERFORMING IN A TRAPPING-DEPENDENT OPERATIONAL MODE

(75) Inventor: Marlin O. Thurston, Columbus, OH (US)

(73) Assignee: Neoprobe Corporation, Dublin, OH (US)

( * ) Notice: Under 35 U.S.C. 154(b), the term of this patent shall be extended for 0 days.

(21) Appl. No.: 09/167,008

(22) Filed: Oct. 6, 1998

(51) Int. Cl.$^7$ ........................................ A61B 5/00
(52) U.S. Cl. ................ 250/370.13; 250/370.01; 250/367
(58) Field of Search .............. 250/370.13, 370.01, 250/367

(56) References Cited

U.S. PATENT DOCUMENTS

| | | |
|---|---|---|
| 4,782,840 | 11/1988 | Martin et al. . |
| 4,801,803 | 1/1989 | Denen et al. . |
| 4,889,991 | 12/1989 | Ramsey et al. . |
| 4,893,013 | 1/1990 | Denen et al. . |
| 5,070,878 | 12/1991 | Denen . |
| 5,151,598 | 9/1992 | Denen . |
| 5,441,050 | 8/1995 | Thurston et al. . |
| 5,475,219 | 12/1995 | Olson . |
| 5,482,040 | 1/1996 | Martin et al. . |
| 5,682,888 | 11/1997 | Olson et al. . |
| 5,732,704 | 3/1998 | Thurston et al. . |
| 6,043,495 | * 3/2000 | Verger et al. ............... 250/370.13 |

OTHER PUBLICATIONS

Butler, et al., "$Cd_x$ $2n_x$ TeGamma Ray Detectors, " Ieee Transactions or Nuclear Science, Santa Fe, N. Mex., 1991.
Morton, et al., "Technical Details of IntraOperative Lymphatic Mapping For Early State Melanoma," Arch. Surg. 1992, 1271 392–999.
Doty, et al., "Properties of Cadmium Zinc Telluride Grown by a High Pressure Bridgeman Method," J. Vac. Sci. Techrol, vol. B10 Jun./Jul., 1992.
Butler, et al., "Recent Developments in Cd Zn Tr Gamma Ray Detector Technology, "Proceedings of the International Symoposium of the SPIE, Santa Fe, N.Mex. Jul. 1992.
Uren, et al., "Lymphoscintigraphy in High Risk Melanoma of the Trunk: Predicting Draining Node Groups, Defining Lymphatic Channels and Locating the Sentinel Node." J. Nuel Med. 1993; 34:1435–1440.
"Lymphatic Mapping and Sentinel Lymphadenectomy For Breast Cancer," Annals of Surgery, vol. 220, No. 3: 391–401, 1994 J. B. Lippincott Company.
Greenson, et al., Identification of Occult Micrometastases in Pericolic Lymph Nodes of Dukes' B Colorectal Cancer Patents Using Mancloral Antibodies Against CytoKeratin and CC49,: Cancer1994; 73: 563–569.
Bertsch, et al., "Radioimmunoguided Surgery System Improves Survival For Patients with Recurrent Colorectal Cancer," Surgery 1995; 118: 634–639.
Arnold, et al., "Radioimmunoguided Surgery in Primary Colorectal Carcinoma: An Intraoperative Diagnostic Tool and Adjuvant to Traditional Staging" American J. Surg 1995; 179: 315–318.
Schneebaum, et al., The Significance of Intraoperative Periportal Lymph Node Metastasis Identification in Patients with Colorectal Carcinoma: Cancer 1995; 75: 2809–2817.
Cote, et al., Intraoperative Detection of Occult Colon Cancer Micrometasis Using $^{125}$I–Radiolabeled Monoclona/Antibody CC49, Cancer 1996; 77: 613–620.
"Semiconductors For Room–Temperature Radiation Detector Applications," Materials research Society Symposium Proceedings, vol. 302 p. 9.

* cited by examiner

Primary Examiner—Constantine Hannaher
Assistant Examiner—Andrew Israel
(74) Attorney, Agent, or Firm—Mueller & Smith LPA

(57) ABSTRACT

A hand-held radiation probe is configured having a crystal thickness as well as a bias generated electrical field which have values to cause the semiconductor crystal to operate in a trapping-dependent operational mode wherein a trapping of substantially all carriers generated by radiation impinging upon the crystal forward face are trapped. The bias level voltage is selected to achieve adequate photopeak heights and to permit the windowing out of lower energy Compton scattering and other noise phenomena.

29 Claims, 13 Drawing Sheets

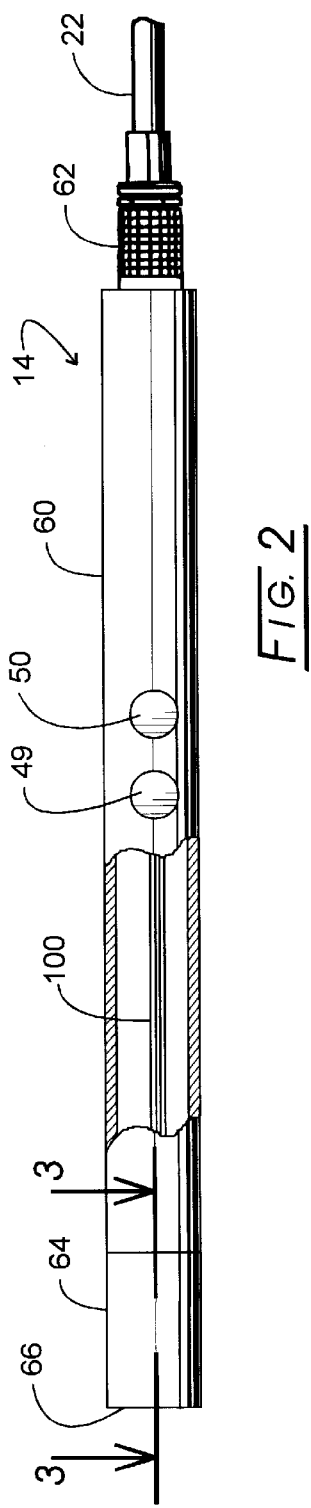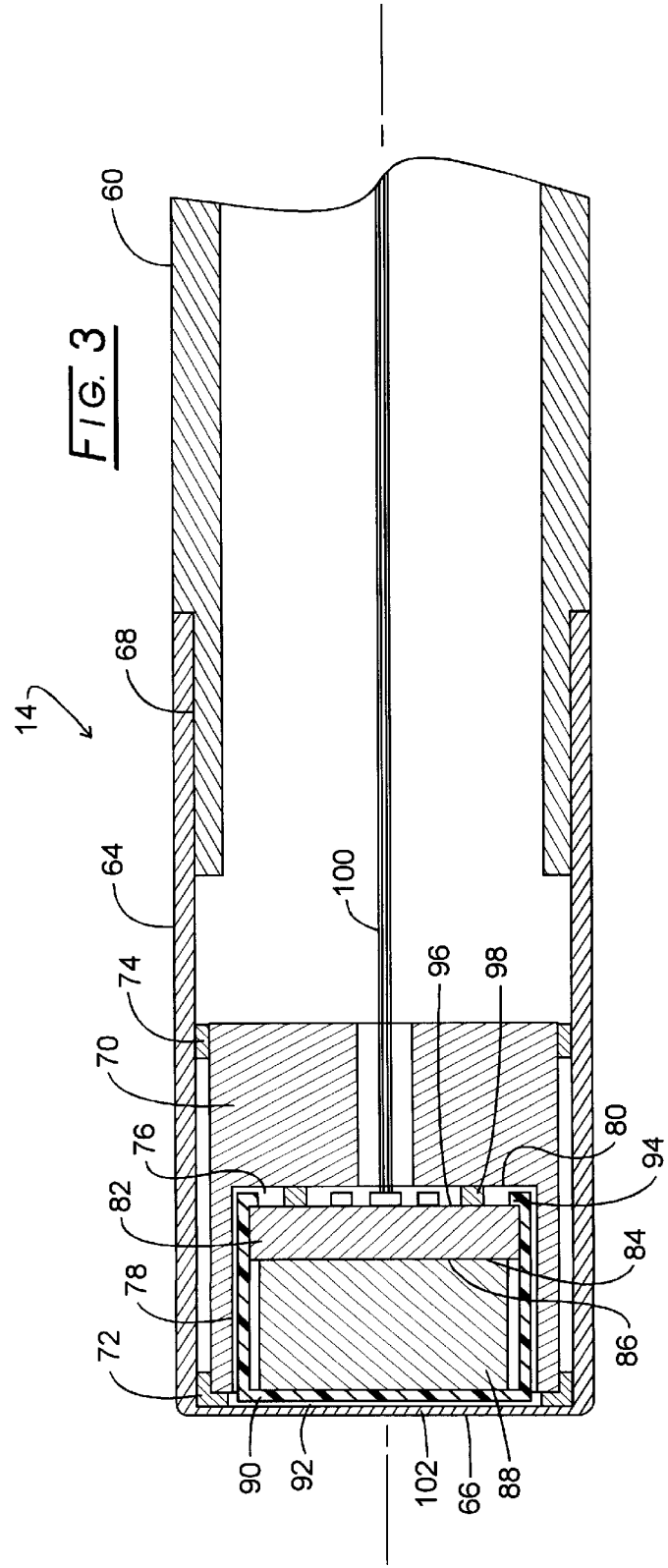

RADIATION PROBE WITH COMPOUND SEMICONDUCTOR CRYSTAL PERFORMING IN A TRAPPING-DEPENDENT OPERATIONAL MODE

CROSS-REFERENCE TO RELATED APPLICATIONS

STATEMENT REGARDING FEDERALLY SPONSORED RESEARCH

Not applicable.

BACKGROUND OF THE INVENTION

Current and historical procedures for treatment of colon and rectal cancer generally have been based upon the natural history of tumor spread, and thence, upon operative and non-operative options available to the practitioner. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) A substantial amount of the effort which has been expended in seeking to aid the surgeon in the process of locating neoplastic tissue has been concerned with the utilization of radiolabeled antibody. For example, one technique includes the scintillation scanning of patients who have been injected with relatively high energy, e.g. $^{131}$I labeled antibodies. Such photoscanning scintigrams are difficult to interpret because of blood pool background radioactivity. Computer subtraction of radioactive blood pool agents and the use of two labeled antibodies (one specific for the tumor and one non-specific) have been attempted in an effort to enhance imaging. Nevertheless, such techniques have been found to provide little, if any, useful information to the surgeon, especially over and above the CAT scan, magnetic resonance imaging, and like traditional techniques. Typically large tumor is readily located by the surgeon by visualization at the operating theater, and, in particular, through palpation, i.e. the feel of tumor as opposed to that of normal tissue. To achieve operative success, however, it is necessary for the surgeon to somehow locate "occult" tumor, i.e. tumor which cannot be found by the conventional surgical procedures of sight and feel. Failure to locate and remove such occult tumor generally will result in the continued growth of cancer in the patient, a condition often referred to as "recurrent" cancer. In general, conventional diagnostic techniques as, for example, use of the classic gamma camera and the like, fail to find or locate occult tumor. As tumor sites become smaller, the radionuclide concentrations at a given site will tend to be lost, from an imaging standpoint, in the background where blood pool radiation necessarily is present in the patient.

In 1984, Martin, M. D., and Thurston, Ph.D., introduced a much improved method for locating, differentiating, and removing neoplasms. Such technique uses a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure now is known as radioimmunoguided surgery (RIGS®) (RIGS being a registered trademark of Neoprobe Corporation of Dublin, Ohio). The RIGS system for surgery additionally is successful because of a recognition that tumor detection should be delayed until the blood pool background of the circulating radiolabeled antibody has had an opportunity to be cleared from the body. As a consequence, the photon emissions or radiation emitted at minute tumors compared to surrounding tissue becomes detectable in view of the proximity of the probe device to it. Fortuitously, the radiolabeled antibody is capable of remaining bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe positioned in close proximity with the tissue under investigation. The seminal patent concerned with the RIGS procedure is U.S. Pat. No. 4,782,840 by Martin and Thurston, entitled "Method for Locating, differentiating, and Removing Neoplasms," issued Nov. 8, 1988, and assigned in common herewith, the disclosure of which is expressly incorporated herein by reference.

The important advances achieved through radioimmunoguided-surgery have been reported. See in this regard, the following publications:

(1) "Radioimmunoguided Surgery System Improves Survival for Patients with Recurrent Colorectal Cancer," Bertsch et al. *Surgery* 1995; 118: 634–639.

(2) "Radioirnmunoguided Surgery in Primary Colorectal Carcinoma:
An Intraoperative Prognostic Tool and Adjuvant to Traditional Staging," Arnold, et al. *American J. Surg.* 1995; 179: 315–318.

(3) "The Significance of Intraoperative Periportal Lymph Node Metastasis Identification in Patients with Colorectal Carcinoma," Schneebaum, et al. *Cancer* 1995; 75: 2809–2817.

(4) "Identification of Occult Micrometastases in Pericolic Lymph Nodes of Dukes' B Colorectal Cancer Patients Using Monoclonal Antibodies against Cytokeratin and CC49," Greenson, et al. *Cancer* 1994; 73: 563–569.

(5) "Intraoperative Detection of Occult Colon Cancer Micrometastases Using $^{125}$I-Radiolabeled Monoclonal Antibody CC49," Cote, et al., *Cancer* 1996; 77: 613–620.

The radioimmunoguided surgical system instrumentation is comprised generally of two basic components, a hand-held probe as described above, which is in electrical communication via a flexible cable with a control console. This control console is located within the operating room facility but out of the sterile field, while the hand-held probe and forward portions of its associated cable are located within that field. The hand-held radiation detecting probe is relatively small and performs in conjunction with a cadmium zinc telluride detector or crystal.

The hand-held probe and preamplification electronics mounted within it in support of the cadmium zinc telluride crystal has been the subject of extensive scientific development. Cadmium zinc telluride crystals are somewhat fragile and exhibit piezoelectric properties which, without rigorous accommodation, will produce deleterious noise phenomena and the like. Further, the crystal and its operatively associated preamplification function are called upon to detect necessarily very faint radiation. In this regard, only a very small amount of radioactive locator will be associated with minute, occult tumor. Thus, radiation emission count rates measured with the RIGS system are relatively low. Research activity concerning the above operational criteria is reflected in the following U.S. Patents.

U.S. Pat. No. 4,801,803 by Denen, Thurston, and Ramsey, entitled "Detector and Localizer for Low Energy Radiation Emissions," issued Jan. 31, 1989.

U.S. Pat. No. 4,893,013 by Denen, Thurston, and Ramsey, entitled "Detector and Localizer for Low Energy Radiation Emissions," issued Jan. 9, 1990.

U.S. Pat. No. 5,070,878 by Denen, entitled "Detector and Localizer for Low Energy Radiation Emissions," issued Dec. 10, 1991.

U.S. Pat. No. 5,151,598 by Denen, entitled "Detector and Localizer for Low Energy Radiation Emissions," issued Sep. 29, 1992.

To derive data representing the presence or absence of occult tumor, a microprocessor-driven complex system of analysis continuously works to statistically evaluate validated counts or gamma strikes to aurally apprise the surgeon of the presence or absence of occult neoplastic tissue. An algorithm under which the noted evaluation takes place is described in U.S. Pat. No. 4,889,991 by Ramsey and Thurston, entitled "Gamma Radiation Detector with Enhanced Signal Treatment," issued Dec. 26, 1989.

The RIGS system, not only having demonstrated its value in locating occult neoplastic tissue, also substantially aids the surgeon in determining the proper staging of the patient in accordance with the extent and severity of the disease. Such staging aids in determining the appropriate post-surgical treatment of patients. In this regard, an effective staging technique utilizing the RIGS system has been described wherein an R Number is determined in accordance with the formula:

$$R\ Number = (n_1 \times E_1)_1 + (n_2 \times E_2)_2 + (n_3 \times E_3)_3 + (n_4 \times E_4)_4$$

wherein each subscript 1–4 represents an anatomic zone, staging of the patient being based upon the R Number determination. See generally, Martin, Jr., U.S. Pat. No. 5,482,040, entitled "Biostaging of Adenocarcinomas Utilizing Radiolabeled Tumor-Associated Glycoprotein Antibodies," issued Jan. 9, 1996.

Cadmium Telluride-based crystals, when employed in conjunction with the RIGS system perform admirably. Advantageously, higher purity levels for the compound crystals are not mandated in order to generate highly acceptable count-based outputs within an energy region of interest. Such performance typically is evaluated in conjunction with a multi-channel analyzer (MCA) relating counts with energy levels of interest. Where a sharp photopeak at the energy level of interest occurs which, in turn, is well spaced from regions of an MCA curve representing a electrical noise, Compton scattering or the like, then windowing or thresholding out of such noise is a straightforward procedure. Cadmium Telluride based crystals achieve this excellent performance, inter alia, because they are used in conjunction with the radionuclide $^{125}$I which exhibits relatively low gamma energy (27–35 Kev). By contrast, the commonly employed $^{131}$I exhibits gamma energy of 360 Kev. The cadmium zinc telluride crystals employed with the RIGS system are, for the purposes of the instant discussion, considered to be "thin", i.e. having a thickness, d, of 2 mm. With the RIGS system, upon the occurrence of a photon event, a generation of carrier pairs generally will take place in a manner wherein holes are trapped at the grounded front face of the crystal. From that position they are immediately collected by the initial integration stage of a signal treatment system. The carrier electrons, traveling at a velocity which is about twelve times greater than the rate of hole migration, all move essentially the same distance such that even if they are trapped they are trapped to the same degree and the result is an excellently performing crystal detection system.

Over the recent past, practitioners have been desirous of utilizing instrumentation similar to the RIGS system in conjunction with higher energy radionuclides. In particular, a call has been made for a Cadmium-Telluride-based hand-held probe device which is operable in conjunction with the use of the radionuclide Technetium 99-m. The latter radionuclide exhibits a gamma energy level of, for example, 140 Kev. That value is somewhat excessive for the cadmium telluride crystal architecture employed with the RIGS system. However, utilization of a hand-held probe with higher energy nuclides for the purpose of lymph system tracking is achieving importance.

The involvement of the lymph system in tumor metastasis has been the subject of extensive investigation and is well established. Lymphatic systems are present as widely dispersed tissues, fluids, and cells concerned in a variety of interrelated functions of the mammalian body including the circulation and modification of tissue fluid formed in the capillary beds, and the removal by mononuclear phagocytes of cell debris and foreign matter. The lymphatic system is importantly involved in participation with the blood vascular system in developing the immune response of the lymphocytes and other cells. Lymph flows within the system as a consequence of a variety of perceived mechanisms of organ and tissue dynamics. For certain cancers, metastasis occurring in consequence of lymph drainage will result in a initial location or positioning of neoplastic cells at certain lymph nodes typically deemed "regional nodes" within a pertinent lymph drainage basin. Some cancers, for example, melanomas, have been observed to exhibit variability in lymphatic drainage patterns emanating from different portions of the body. Other cancers, such as those encountered in the breast will evidence somewhat more predictable nodal involvement. In designing forms of cancer disease management, therefore, efforts are directed to the identification of affected lymph nodes. For melanomas, it has been a more recent practice to identify the pertinent drainage basin or regional nodes along with an evaluation of the extent of lymph involvement with micrometastasis. A presurgical step undertaken in about 20% of investigational procedures concerning melanomas looks to carrying out of a gamma camera generated form of lymphoscintigraphy which gives the clinician a gross two-dimensionally limited image, generally showing the tumor site injection of sulfur colloid labeled with Technetium 99-m ($^{99m}$Tc) and, spaced therefrom, a region of radioactivity at the pertinent regional lymph nodes. The latter information at least confirms the path of drainage and the location of the proper drainage basin. Regional nodes then are removed and submitted for pathology evaluation.

For cancers such as breast cancer, the sites of lymph node involvement are commonly encountered at axillary, internal mairunary, and supraclavicular lymph node regions. Of these, the axillary lymph node region is the principal site of regional metastasis from carcinoma of the breast, and approximately 40% of patients have evidence of spread to the axillary nodes. In early approaches to the disease, these axillary nodes were removed as a form of therapy. Presently, however, their positive involvement, or lack thereof, has become the subject of diagnostics as opposed to therapy. In this regard, the combination of the presence and extent of metastasis to the axilla represents the single most important prognostic factor for the management of patients with breast cancer. See generally "Cancer, Principles and Practice of Oncology," vol. 1, 4th ed. DeVita, Jr., et al., chapter 40, Harris, et al., J.P. Lippincott Co., Philadelphia, Pa. (1993).

The axilla is a triangular region bounded by the axillary vein superiorly, the latissimus dorsi laterally, and the serratus anterior medially. With more current diagnostic procedures, essentially all axillary nodes at the axilla assumed to represent the drainage basin are removed during surgery for analysis. In general, somewhere between 10 and 30 nodes will be removed in the course of dissection with, of course, the attendant risks. In this regard, these nodes are generally surrounded by investment or fatty tissue and visualization of them necessarily is limited. Such dissection will pose risks of cutting the long thoracic nerve, the thoracic-dorsal nerve, the nerve to the pecto-alis major or the axillary vein. Morbidity may occur in some cases due to regional node removal and patients are known to frequently discuss a numbing of the arm region following the procedure.

While this form of somewhat radical axillary lymph node dissection has been the conventional approach to determining nodal metastatic involvement, more recent data suggests that less radical axillary node evaluation procedures may generate equivalent information for staging and patient management, but with far more limited dissection and resultant trauma, as discussed below.

Patient management for staging purposes for the case of cutaneous melanoma is highly predicated upon determinations of lymph involvement. A number of factors are involved in the prognosis of the disease, including, inter alia, location, tumor thickness, level of invasion, growth patterns, and of particular importance the identification of regional node metastatic involvement. Generally, surgical excision of metastatic nodes within the drainage basin of a lesion has been considered the only effective treatment for cure or disease control. Some investigators have preferred to excise only clinically demonstrable metastatic nodes associated with the lesion, while others have chosen to excise the nodes even where they may appear normal because of the risk of the presence of occult (clinically undetectable) metastasis. A substantial dialog has been carried on by investigators as to whether or not elective lymph node dissection or lymphadenectomy is an appropriate therapy. Elective lymphadenectomy has the major advantage of treating a nodal metastasis at a relatively early stage in its natural history when the tumor burden is low. On the other hand, such an approach may subject patients to surgery which would otherwise have been unnecessary. In particular, where patients exhibit a clinical Stage I level of the disease, there will be no nodal metastasis present and no benefit then can be realized from regional lymphadenectomy.

Morton, et al., undertook an investigation of a procedure designed to identify that lymph node nearest the site of a melanoma and within the pertinent lymph drainage basin. Such a node, being on the most direct drainage pathway will present the most likely site of early metastasis and is referred to as the "sentinel node." Thus, by carrying out only a limited dissection specific to this node and performing pathologic analysis of it, staging can be achieved without at least initial resort to more radical lymphadenectomy. With the approach, once the drainage basin from a lesion is identified, for example, by lymphoscintigraphy, an intraoperative mapping of the cutaneous lymphatics with vital dye is carried out at the time of surgical removal of the primary lesion. The vital dye, for example of blue color, is injected at the site of the lesion and tracked by blunt dissection until the sentinel node is reached. That node is now exclusively of blue color and readily identified. Thus, the sentinel draining lymph node of each primary melanoma is isolated and removed. By examining the sentinel nodes, for example by frozen section using routine hematoxylin-eosin histopathological techniques, as well as rapid immunohistochemical techniques, only those patients who have evidence of micrometastasis in the sentinel draining node are subject to subsequent lymphadenectomy. See generally, Morton D., Wen D-R, Wong J., et al. "Technical Details of Intraoperative Lymphatic Mapping for Early Stage Melanoma," Arch. Surg. 1992: 127:392–399; and "Lymphoscintigraphy in High-Risk Melanoma of the Trunk: Predicting Draining Node Groups, Defining Lymphatic Channels and Locating the Sentinel Node," R. F. Uren, et. al, J. Nucl Med 1993; 34:1435–1440.

The approach of Morton, et al., also has been undertaken to moderate the otherwise somewhat radical axillary lymph node dissection common in staging breast cancer. Through the utilization of the noted vital dyes in conjunction with the lymph drainage system from primary breast tumor, less radical sentinel node based procedures may result in adequate axillary staging and regional control. With the procedure, in general, a vital blue dye is injected into the breast mass and surrounding breast parenchyma. Following a relatively short interval, a transverse incision is made just below the hair bearing region of the axilla. Blunt dissection is performed until a lymphatic tract or duct leading to a blue stained node is identified. The lymph duct, having a blue color, provides a guide path leading to the location of the most proximal lymph node and thus the sentinel node. This sentinel node is excised and evaluated. While the procedure calls for considerable surgical experience and talent associated with the delicate task of following the blue duct (a ruptured dye-carrying duct can be problematic), the ability to identify a tumor-free sentinel lymph node will enable the surgeon to accurately stage metastasis-free breast cancer patients without subjecting them to the risks of radical dissection. The approach may also improve histologic staging by enabling the pathologist to focus on fewer lymph nodes. See generally Guiliano, A. E.; Kirgan, B. M.; Guenther, J. M.; and Morton, D. L., "Lymphatic Mapping and Sentinel Lymphadenectomy for Breast Cancer," Annals of Surgery, vol. 220, no. 3: 391–401, 1994, J.B. Lippincott Company.

As a replacement for or an adjunct to the tracking of portions of the lymph system to locate a sentinel lymph node, practitioners have injected the noted sulfur colloid labeled with $^{99m}$Tc technician at the site of the lesion. Then, employing a hand-held radiation detecting probe, migration of the injectate along the lymph ducts to the sentinel node is carried out. Thurston, et.al, in U.S. Pat. No. 5,732,704 entitled "Radiation Based Method for Locating and Differentiating Sentinel Nodes," issued Mar. 31, 1998, describe an improved technique for thus tracking a lymph duct and for utilizing a thresholding procedure three dimensionally finding a sentinel lymph node containing radiopharmeceutical with a hand-held probe. An improved apparatus and system for carrying out this procedure us described by Thurston and Olson in an application for U.S. Pat. Ser. No. 08/543,032 filed Oct. 13, 1995 now U.S. Pat. No. 5,857,463, issued Jan. 12, 1999 and entitled: "Remotely Controlled Apparatus and System for Tracking and Locating a Source of Photo Emissions."

BRIEF SUMMARY OF THE INVENTION

The present invention is addressed to a hand-held radiation probe suited for medical applications. Using the compound semiconductor, cadmium telluride, the probe is capable of detecting and locating relatively higher gamma energy radionuclides such as $^{99m}$Tc. The latter radionuclide exhibits a gamma energy level of 140 Kev. Performance with desirably sharp photopeaks as evidenced in multi-channel analyzer plots, is achieved by operating these room temperature performing crystals in a trapping dependent mode wherein a trapping of substantially all carriers occurs within the volume of the semiconductor. Advantageously, this mode of performance does not require costly, very high purity semi-conductor crystal structures.

To derive this operational mode, the thickness of the semiconductor crystals is selected to achieve trapping electron-hole pairs created by all ionizing radiation interactions exciting bound electrons. Further, the electric field or bias imposed across the thickness of the semiconductor crystal is made relatively lower to promote this trapping. The result is to derive good count efficiency with a very good windowing of background including Compton scattering phenomena.

As another aspect of the invention, by appropriately selecting the bias voltage level, the hand-held probes also can be utilized in medical procedures employing locators labeled with relatively low gamma energy radionuclides as are used, for example, in the RIGS procedure. Thus, the windowing or validation and preamplification function of the controller circuitry of the RIGS procedure may be employed with such procedures as lymph duct mapping and sentinel lymph node dissection.

Other objects of the invention will, in part, be obvious and will, in part, appear hereinafter. The invention, accordingly, comprises the apparatus, system, and method possessing the construction, combination of elements, steps and arrangement of parts which are exemplified in the following description.

For a fuller understanding of the nature and objects of the invention, reference should be had to the following detailed description taken in connection with the accompanying drawings.

BRIEF DESCRIPTION OF THE DRAWINGS

FIG. 2 is a side view of a hand-held probe shown in FIG. 1 with portions broken away to reveal internal structure;

FIG. 3 is a sectional view taken through the plane 3—3 in FIG. 2;

DETAILED DESCRIPTION OF THE INVENTION

In the discourse to follow the hand-held probe system of the invention will be seen to be configured with a cadmium telluride crystal architecture and crystal biasing arrangement which combine to derive a trapping dependent operational mode wherein a trapping of substantially all photon event derived carriers generated by gamma radiation is realized. With such an arrangement, the system may be used in the conventional manner in carrying out RIGS surgery wherein the locator, tagged with relatively low energy gaima radiation is systemically injected. However, such a probe is particularly suited, with appropriate windowing, to carry out lymph node mapping utilizing higher energy gamma radiation, for example, $^{99m}$Tc at 140 Kev. For that application, a radiopharmaceutical is not systemically injected but is simply injected in the vicinity of a lesion. For either of these alternate modes of operation, count photopeaks are realized which are readily isolated by the windowing function of the system's control circuitry.

CdTe crystals may be alloyed and still are referred to as "cadmium telluride" or "CdTe" crystals for present purposes. A preferred cadmium telluride crystal as described in commonly-assigned U.S. Pat. No. 5,441,050, issued Aug. 15, 1995, is CdTe material alloyed with zinc and generally represented by the expression: $Cd^1_xZn_xTe$. In general, CdTe detecting crystals exhibit benefits such as operability at room temperature, high counting rates and small size. The proportioning of the Cd component and Zn component of the crystals may vary to provide an effective ratio selected to suit the particular requirements of the user. However, a lower limit or boundary for the proportion of zinc wherein x equals about 0.2 has been determined. Information concerning the alloyed crystals is provided in the following publications:

Butler, Lingren and Doty, "$Cd_{1-x}Zn_xTe$ Gamma Ray Detectors," IEEE Transactions on Nuclear Science, Santa Fe, N.Mex., 1991

Butler, Doty and Lingren, "Recent Developments in CdZnTe Gamma Ray Detector Technology," Proceedings of the International Symposium of the SPIE, Santa Fe, N.Mex., July, 1992

Doty, Butler, Schetziaa and Bowers, "Properties of Cadmium Zinc Telluride Grown by a High Pressure Bridgman Method," J. Vac. Sci. Technol., Vol. B10, June/July, 1992.

Figure 1:
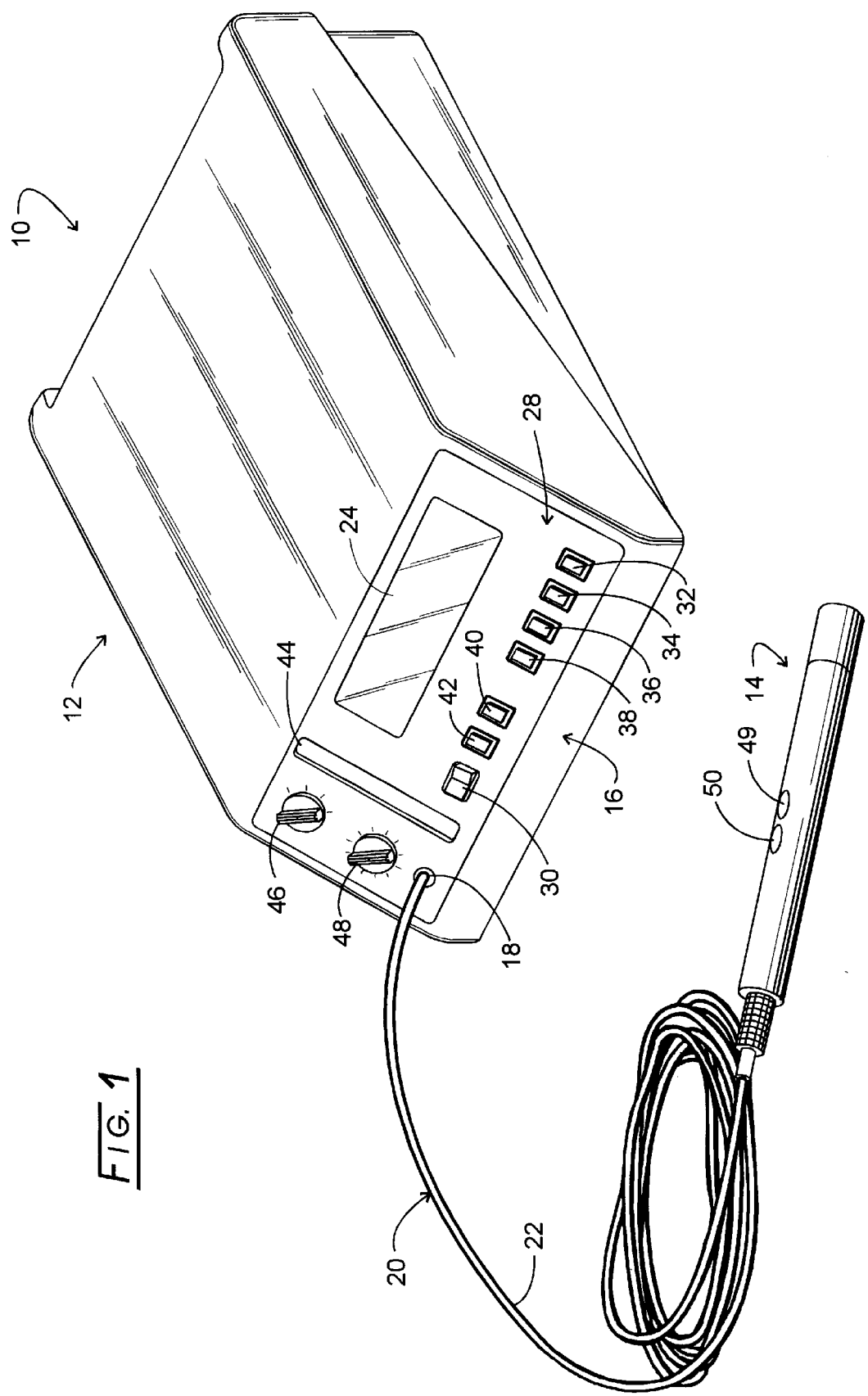
FIG. 1 is a pictorial representation of the system and instrumentation of the invention.

Referring to FIG. 1, surgical apparatus and system for alternately locating and differentiating relatively low gamma energy radionuclides as well as a relatively higher gamma energy non-systemically injected radiopharmaceutical is represented generally at 10. The apparatus and system 10 includes a control assembly or console 12 to which is coupled a probe instrument represented generally at 14. The control console 12 is configured for both carrying out radioimmunoguided surgery (RIGS) and for tracking radiopharmaceuticals injected at the site of a tumor to locate a sentinel lymph node. In the latter regard, the photon count evaluation, including lower threshold validation or windowing and discriminator functions of the RIGS system are commonly utilized. That system is described, for example, in U.S. Pat. No. 4,801,803, entitled "Detector and Localizer for Low Energy Radiation Emissions," by Denen, Thurston, and Ramsey issued Jan. 31, 1989 and assigned in common herewith. The forward face 16 of console 12 includes a coupling or connector 18 which provides for electrical signal communication and power supply association with the probe instrument 14 via a transmission assembly represented generally at 20 which includes a flexible cable 22. This cable implementation of the transmission assembly is a preferred arrangement for such transmission functions, however, other approaches will occur to those skilled in the art. Forward face 16 of console 12 additionally carries a relatively large liquid crystal display (LCD) or readout 24, as well as an array of push-type switches 28. This array of switches permits the microprocessor driven control system to carry out an instructive or "user friendly" dialog with the practitioner. In addition to a conventional on and off rocker switch 30, the switches provided at forward face 16 include such function selection switches as a count mode switch 32, a reset count switch 34, a background count or squelch switch 36, a sound control switch 38, and down and up incrementing switches shown respectively at 40 and 42.

Also mounted at the forward face 16 of the console 12 are components dedicated to the lymph tracking features of the system 10. In this regard, a linear, segmented LED array 44 is included for the purposes of providing a visual cuing aspect as to peak count rate level. A range selection switch is provided at 46. Switch 46 permits the practitioner to select any of four count rate ranges to achieve full scale readouts. These ranges may, for example, be 0–100 counts per second; 20–1,000 counts per second; 50–2,500 counts per second; 100–7,500 counts per second; and 600–30,000 counts per second. Below the knob actuated range switch 46 is a knob actuated threshold control 48 which is used to provide a count rate threshold input which is a percentage evaluation of any one of the count rate ranges established at switch 46. This thresholding is a variation of the background count or squelch procedures carried out in connection with switches 36 and 34. In this regard, the function of reset count switch 34 is to derive a count value over a preset interval, for example, two seconds. The background count switch 36 is employed in conjunction with reset count switch 34 to develop a statistical count value based upon a measured background count rate. For example, in the RIGS procedure, a targeting agent is systemically injected and the probe instrument 14 initially is positioned in the vicinity of the heart or aorta in order to obtain a blood pool background count rate. The interval during which this rate is determined is, for example, five seconds. The microprocessor-based control system of console 12 then calculates a statistically significant value, for example, a predetermined number of standard deviations of the basic background count rate to derive a statistically significant threshold radiation count rate level. This, for example, may be three sigma above the base count rate. The ranging procedure is referred to by surgeons as "squelching." Operating in conjunction with that threshold level in the RIGS procedure, the system 10 provides the surgeon with audible cues indicating that a high probability of tumor involvement is present at a location closely adjacent the position of the forward window of probe instrument 14. This squelching procedure also may be utilized in conjunction with the detecting and locating of sentinel lymph nodes in connection with breast cancer or melanoma studies or procedures. However, with the system 10, a dedicated adjunct system is provided for that purpose. Not shown in FIG. 1 is a mode selection switch which is manually actuated between two positions, one electing that system 10 operate in a standard RIGS mode, and the other electing that the system 10 operate in conjunction with an adjunct system for carrying out sentinel node detection procedures and the like. Two switches are provided on probe 14 as at 49 and 50 which afford the practitioner the opportunity to carry out the function otherwise carried out by threshold setting control 48. In general, where switches as in 49 and 50 are not provided with the probe 14, then the control 48 is utilized for a threshold setting. Remote switching suited for probes as at 14 is described, for example, in U.S. Pat. No. 5,682,888, issued Nov. 4, 1997 by Olson and Thurston entitled "Apparatus and System for Detecting and Locating Photon Emissions with Remote Switch Control."

Turning to FIGS. 2 and 3, the probe 14 is illustrated at a greater level of detail. In FIG. 2, the probe is seen to have a cylindrical housing 60 formed, for example, of a chromium plated aluminum. The rearward portion of housing 60 is configured having a multiple pin connector 62 by which the electrical connection is made with cable 22. Forwardly, the probe 14 is formed having a chromium plated aluminum cap 64 which, in turn, extends to a thin aluminum window 66. FIG. 3 reveals the internal structure of the probe 14 in the vicinity of the cap 64. In this regard, the cap 64 is connected to the housing 60 at a step-down portion 68 thereof. Connection is made, for example, utilizing an electrically conductive epoxy adhesive. Mounted within the cap 64 is a radiation blocking tungsten crystal mount 70. Mount 70 is suspended within the cap 64 by microporous foam rings 72 and 74 thus, the component 70 and the crystal mounting portions thereof are suspended between damped, vibration avoiding foam supports. A cylindrical cavity 76 is formed centrally within the mount 70, having side walls 78 and an end wall 80. Located somewhat adjacent end wall 80 is a disc shaped rigid circuit board 82. Formed, for example of alumina, the circuit board 82 is configured having a gold coated forward surface 84 which is retained in intimate, compressive compact with the rearward face 86 of a cadmium telluride crystal 88. Crystal 88 is retained in compression against the forward surface 84 of circuit board 82 by a cylindrical polymeric retainer cap 90. The forward wall of retainer cap 90 at 92 is formed having a slight inward or concave configuration, while the cylindrical side walls thereof are configured with an angular latch portion 94. Latch portion 94 snaps over the rearward surface 96 of circuit board 82. The interior surface of the retainer cap 90 is coated, for example, with gold, and it is through this coating that ground is applied to the forward surface 84 of crystal 88. Such ground is conveyed from the circuitry which is mounted on the rearward face 96 of circuit board 82. To accomodate for the surface mount components thereon, the rear face 96 is supported upon an annular standoff 98 which is coupled to crystal mount 70. Electrical communication with the crystal and circuit mounted upon circuit board 82 is by leads 100.

It may be observed that the cadmium zinc telluride crystal 88 is relatively thick, having a thickness distance, d, of 4 mm. In its operation, bias is applied across the crystal 88, ground being applied at its forward face and plus voltage, for example, 60 volts being applied from the forward surface 84 of circuit board 82. Note that the forward wall 92 of the polymeric cap 90 is slightly spaced from the inside surface of window 66. This provides a gap for the purpose of avoiding vibrationally induced noise phenomena at the crystal 88.

Figure 4A:
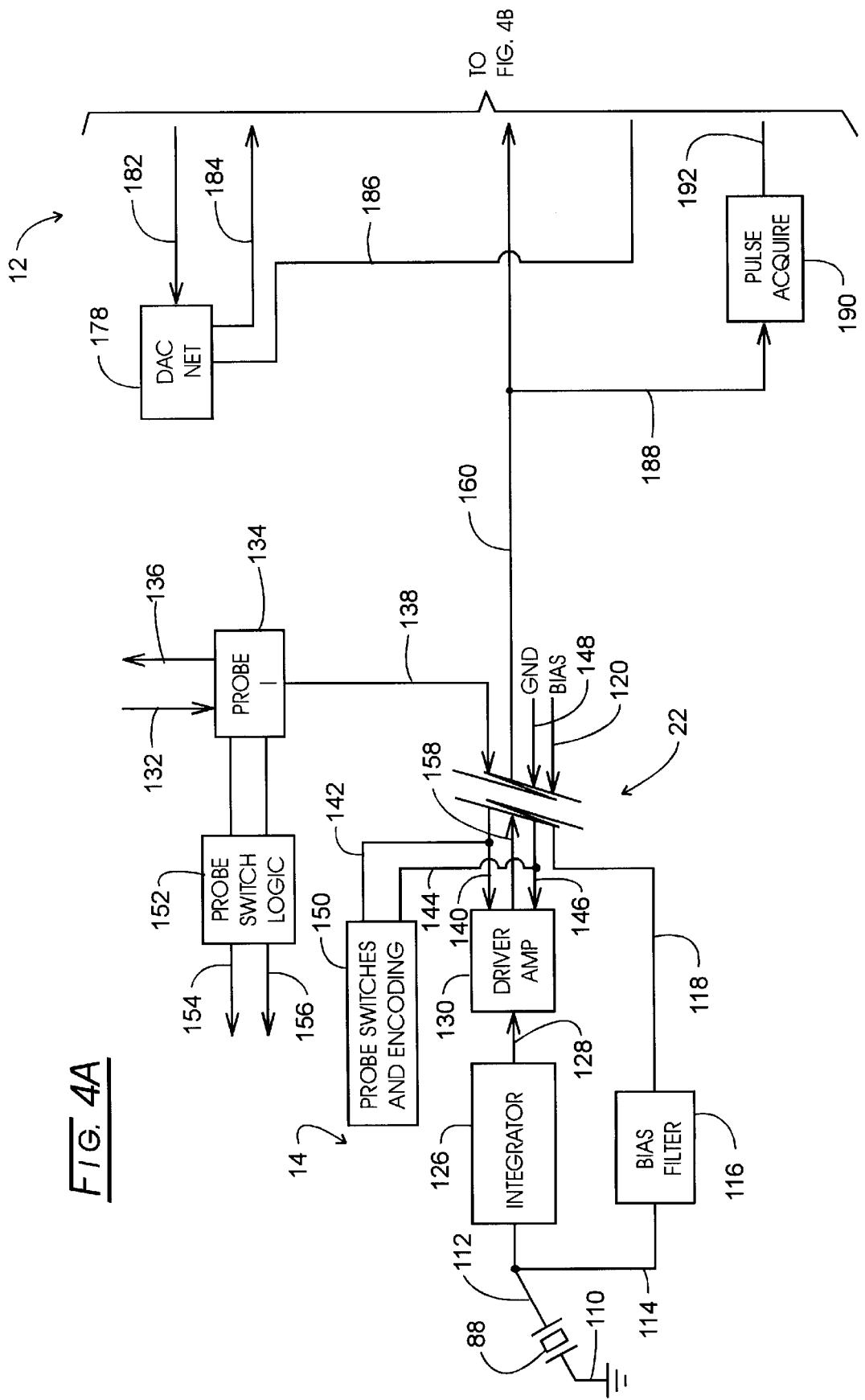
FIGS. 4A and 4B combine as labeled thereon to provide a block diagrammatic representation of the circuits employed with the control assembly and probe shown in FIG. 1.
Figure 4B:
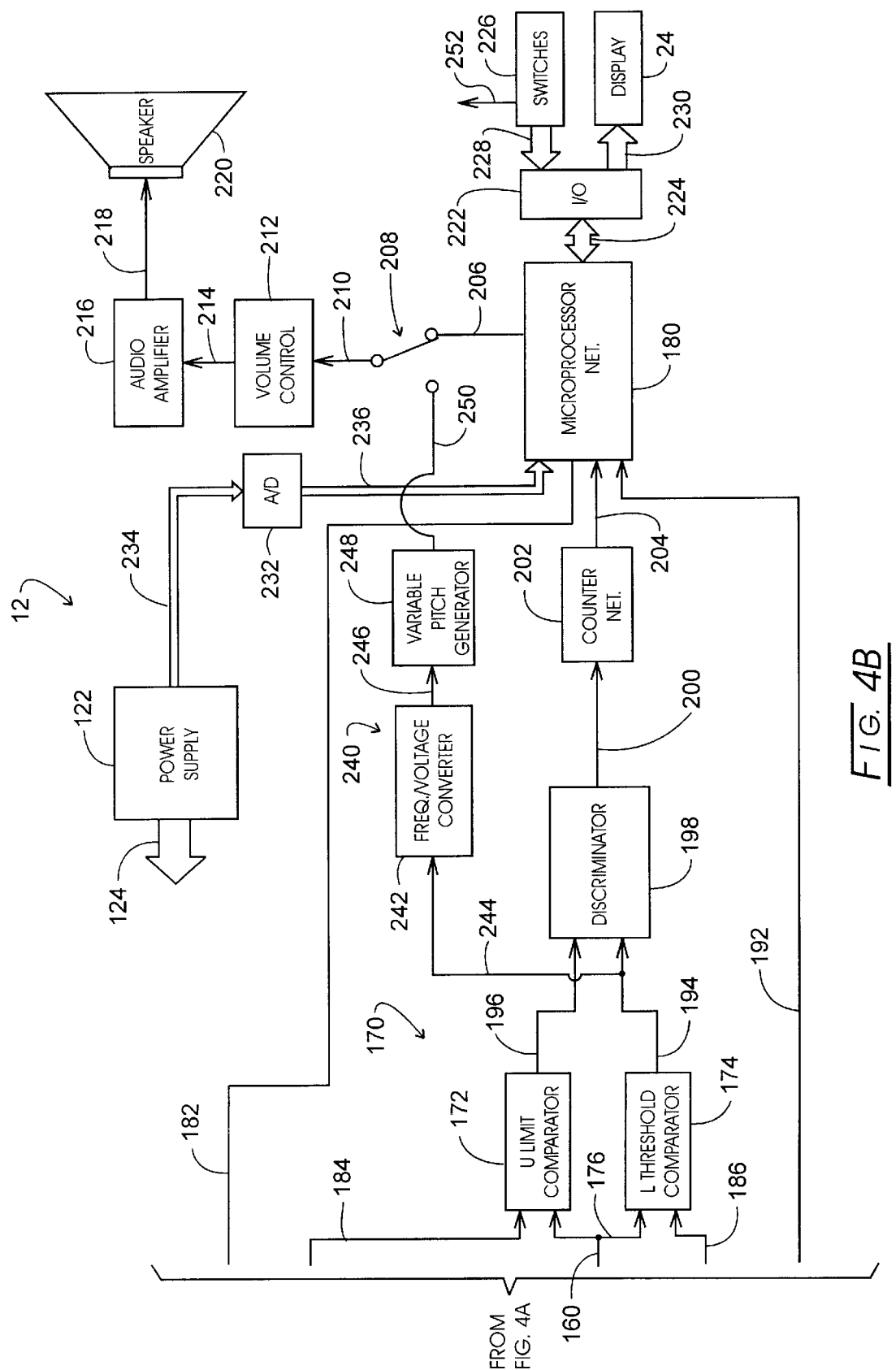

Referring to FIGS. 4A and 4B, a block diagrammatic representation of the circuitry employed with the system 10 is provided. These figures should be considered in mutual adjacency in the manner labeled thereon. In FIG. 4A, the cadmium telluride crystal 88 reappears symbolically with the same numeration. Crystal 88 is shown having its forward face coupled to ground, as represented by a line 110 while the opposite, face thereof is represented as having a positive bias applied thereto from a line 112. It may be recalled that the forward face grounding is provided from a gold coating on the interior of retainer cap 90 and a corresponding gold coating at the forward face surface 84 of circuit board 82. Line 112 is seen coupled via line 114 to a bias filter represented at block 116. The input to filter 116 is represented at line 118 as being applied through the cable described earlier at 22 and leads 100. Cable 22 also is represented generally in the instant figure. The bias input as represented at line 120, emanates from a multi-output power supply shown in FIG. 4B at block 122. These various outputs of the power supply 122 are represented, in general, by an arrow 124 extending from block 122.

Returning to FIG. 4A, line 112 extending from the crystal 88, carrying a count related charge output corresponding with radiation emissions impinging upon the crystal 88, is seen to extend to an integrator stage represented at block 126. This integrator stage 126 forms part of the pre-amplification function mounted at circuit board 82. The integrated valuation of detected radiation then is shown directed as, represented by line 128 to a driver amplification network shown at block 130. Such a pre-amplification circuit comprised of blocks 126 and 130 is described in U.S. Pat. No. 5,441,050 by Thurston and Olson, issued Aug. 15, 1995, entitled: "Radiation Responsive Surgical Instrument." A d.c. power supply is provided from the power supply represented at block 122 and arrow 124 (FIG. 4B) for the pre-amplification function. This power supply is directed, as represented at line 132, to a probe current network represented at block 134. Under microcomputer control, as represented at line 136, the network 143 develops signals, for example, determining whether the probe instrument 14 has been properly connected to the console 12. Delivery of the d.c. power supply for the pre-amplification function is represented at lines 138 and 140. Line 140 forms a component of flexible cable 22. As described in the U.S. Pat. No. 5,682,888, (supra) the probe switches 49 and 50 may be of a piezoelectric variety. Accordingly, connected with line 140 is one line of the switch outputs as represented at line 142. The second line from the switching network is connected as represented by line 144 to ground at line 146. This ground is provided from the power supply as represented at block 122, and is represented by an additional line 148 within the cable 22. Probe switches and an associated encoding circuitry are represented in FIG. 4A at block 150. In general, when either of the switches 49 or 50 is actuated, a switch voltage signal is generated which is directed to a current deriving voltage comparator circuit having an output coupled, as represented at line 142, with the power supply input line 138. The switch voltage signal generated by the piezoelectric switches, performing with such a comparator circuit, functions to impose a current signal of predetermined amplitude at lines 140 and 146, which is detected by probe switch logic circuitry represented at block 152. The logic represented at block 152 includes a monitoring amplifier stage and level comparator circuit which function to provide switch input signals corresponding with the actuation of either of the switch components 49 or 50. These switching input signals are provided, respectively, at lines 154 and 156. With this implementation of the probe switches as represented at block 150, as well as the probe switch logic represented at block 152, the preexisting power supply line of flexible cable 22 is utilized to carry the switch signals and no additional wiring is required for that component of the system 10.

The pre-amplification stage forms part of a signal treatment function which ultimately develops count signals. In this regard, the output of the pre-amplification circuit at line 158 is conveyed via cable 22 for introduction to the control assembly 12, the corresponding signal carrying line of which is represented at line 160. Line 160 extends to the input of an energy window network represented in FIG. 4B in general at 170. Network 170 functions to evaluate the count based outputs at line 160 in terms of gamma energy levels of interest to derive validated photon count signals. It may be observed that the energy window network 170 includes an upper limit comparator represented at block 172, as well as a lower threshold comparator represented at block 174. The count output signals, which will include varieties of noise, including Compton scattering based phenomena for the high energy mode of operation, are submitted simultaneously to each of these comparator functions 172 and 174 as represented at lines 176 and 160. Correspondingly, the comparison values or limits associated with the upper limit comparator 172 are applied from a digital-to-analog converter (DAC) seen in FIG. 4A at block 178. Converter 178 is under the control of a microprocessor network represented at block 180 (FIG. 4B), such digital control to device 178 being asserted as represented at line 182. Thus, the upper limit value asserted at comparator 172 is provided at line 184 from DAC 178. Correspondingly, the lower threshold value for comparator function 174 is asserted from DAC 178 via line 186. FIG. 4A also reveals that signals at line 160 are directed, as represented at line 188, to a pulse acquire function represented at block 190. Network 190 functions, when activated by the microprocessor function 180, to acquire the value of the highest pulse amplitude witnessed at line 160. Periodically, this information is transmitted to the microprocessor function 180 as represented by line 192. Representing a form of peak detector, the network 190 sometimes is referred to as a "snapshot circuit."

With appropriate operation of the semiconductor crystal 88 of the probe 14 assemblage, it is possible to observe a distinct voltage output pulse from the preamplifier or forward signal treatment components for each interacting radiation quantum (photon or fast particle) that deposits a significant amount of energy in the detector 88 volume. Under such circumstances, the amplitude of the output pulse reflects the induced charge from the detector which is often an indicator of the initial energy of the individual quantum. The incoming signals additionally may represent spurious phenomena such as cosmic rays and the like, and for sentinel node identification applications, the incoming signals also typically will include a Compton scattering form of noise. Accordingly, the energies of the incoming signals are evaluated at the energy window network 170 as seen in FIG. 4B.

The lower threshold comparator function 174 will promulgate a pulse at line 194 when the signal asserted thereat exhibits an amplitude of value equal to or above a threshold value established, as noted above, from line 186. Correspondingly, the signals at line 176 will be evaluated by the upper limit comparator function 172 such that when the incoming signal exhibits an amplitude of value above the upper limit value established from line 184, a pulse will be promulgated at line 196. For the RIGS component of the system 10, outputs from lines 194 and 196 then are directed to the input of an asynchronous, sequential, fundamental mode discriminator circuit represented at block 198. Circuits as at block 198, while being sequential in nature, are not synchronized in any way with a clock signal. Such circuits as at block 198 are described in U.S. Pat. No. 5,475,219 by Olson, entitled "Validation of Photon Emission-Based Signals Using an Energy Window Network in Conjunction with a Fundamental Mode Discriminnator Circuit," issued Dec. 12, 1995. The discriminator function represented at block 198 serves to generate count signals in the form of finite pulses at line 200. Such pulses occur in the presence of the signal at line 160 which represents a photon emission which is valid from the standpoint of the gamma energy range of interest associated with it.

The pulsed signals at line 200 are provided to a counter network represented at block 202. These pulses at line 200 are counted by the network 202, whereupon, as represented at line 204, count data is submitted to the microprocessor network 180 for statistical analysis. The function of counter network 202 may be implemented in software as described in the above-referenced U.S. Pat. No. 4,889,991. Microprocessor network 180 performs under a variety of operational modes, depending upon the user inputs to the functions switches at array 28 as well as to a calibration input. In general, it functions to provide outputs to two output components, one aural type generated from a speaker, and the other a visual output at display 44. Generally, a "siren" type of signal manifested with a predetermined frequency variation is asserted as represented by line 206 through a mode switch represented at 208 and line 210 to a volume control function represented at block 212, whereupon the volume adjusted signal is directed, as represented at line 214, to an audio amplification circuit represented at block 216. The circuit at block 216, in turn, as represented at line 218, drives a speaker 220. With the noted siren arrangement, the frequency output from speaker 220 increases with an exponential change from 20 Hz to 1200 Hz when the average count rate determined by system 10 exceeds a preset threshold level which is statistically significant over background count rates. The siren mode is accessed by the user from console 12 by sequentially actuating switch 36 then switch 34. This siren mode of performance is described in detail in the above-referenced U.S. Pat. No. 4,889,991, by Ramsey and Thurston.

Microprocessor network 180 performs in conventional fashion with an input/output network as represented at block 222 and dual directional arrow 224. This input/output port function 222 provides for appropriate scanning of peilinant console 12 mounted switches as represented at block 226 and arrow 228. The output port also drives the display 24, again identified by the same numeration but shown in block fonn, as represented by arrow 230. Further, microprocessor network 180 may be employed to monitor the performance of the power supply represented at block 122. This is shown as being carried out by the interaction of the microprocessor network 180 with an analog-to-digital converter represented at block 232 and having an association represented by arrows 234 and 236. The converter 232 functions to digitize analog values at the power supply 122 for submittal to microprocessor network 180.

Components of the lymph node mapping or high gamma energy aspects of system 10 are represented at 240 in FIG. 4B. The components of this adjunct system 240 include a frequency-to-voltage converter represented at block 242 which responds to the count associated signals from the lower threshold comparator at block 174 as represented at lines 194 and 244 to provide a rate level signal corresponding with the frequency of those count associated signals at line 246. This signal will be provided as a d.c. voltage level which extends within a dynamic range of, for example, zero to 2.5 volts. That signal then is directed to a variable pitch generator function represented at block 248. The function at block 248 serves to provide the noted initial ranging feature and a count rate thresholding feature which may be controlled from knob 48 or the up/down switches 42 and 40 (FIG. 1). Additionally included in the function 248 is a post thresholding amplification network having a gain corresponding with the threshold level value to permit full scale performance of the speaker 220 and linear LED array 44 (FIG. 1). The output of function 248 is shown at line 250 extending to one terminal of switch 208. Microprocessor network 180 continues to provide volume control during the operation of generator function 248 in response to actuation of switch 38 (FIG. 1). An output represented at arrow 252 will be seen to extend to a "beep" generator which provides an auxiliary audible switch feedback for the user.

Figure 5:
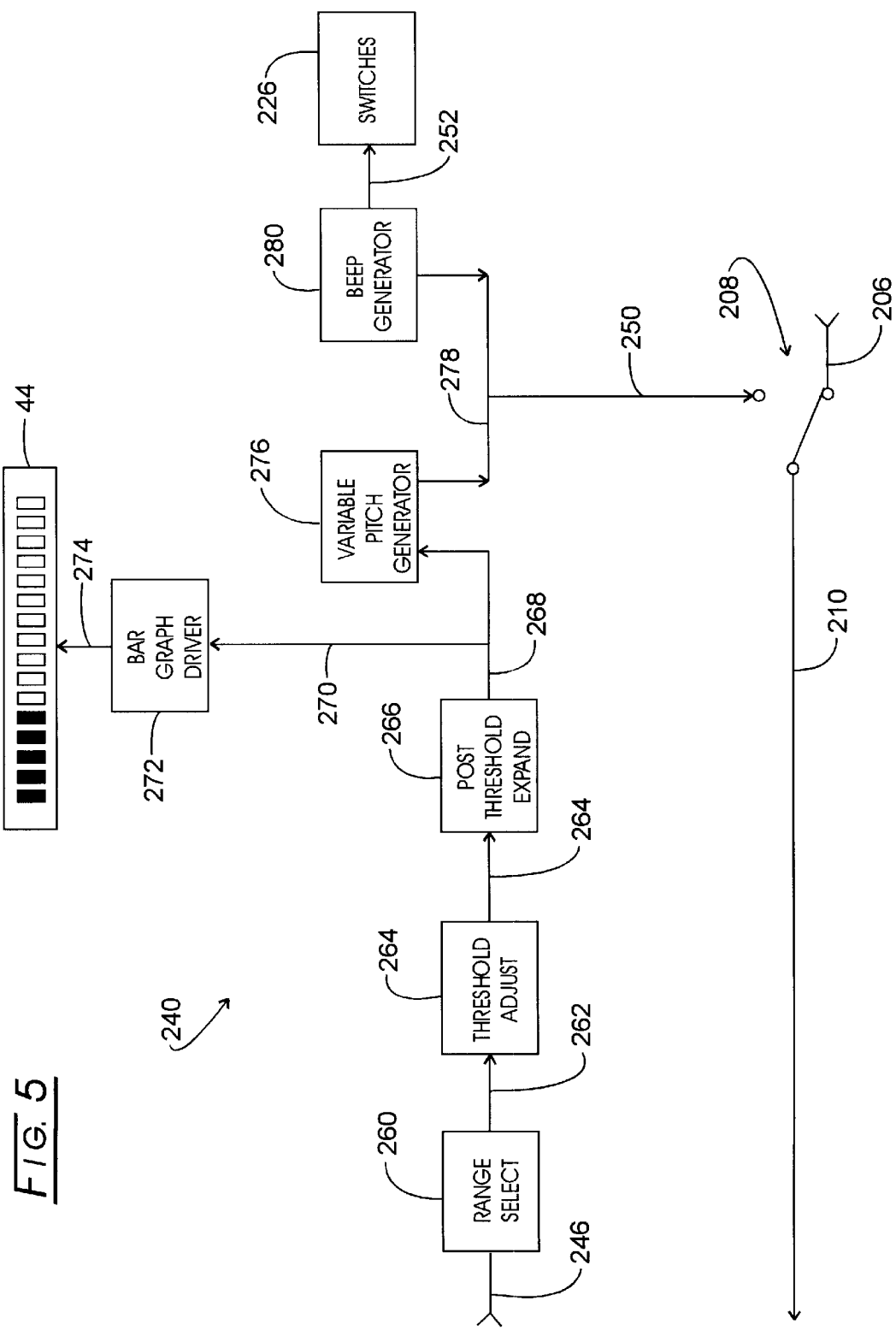
FIG. 5 is a block diagram showing variable pitch generator components of the system of the invention.

Referring to FIG. 5, a block diagrammatic representation of the generator function 248 is provided. The figure reveals that the output from the converter network 240 at line 246 is directed to a range select function represented at block 260. Function 260 provides for the earlier-described selection of ranges of counts per seconds such that an initial approach is taken to derive full scale drives for the visual and aural cuing components, i.e., LED array 44 and speaker 220. Upon selecting an appropriate range, the range adjusted signal level is directed, as represented at line 262 to the input of a threshold network represented at block 264. At block 264, a threshold is established with respect to the incoming signal at line 262 which represents a percentage of full scale or full dynamic range of that signal. Additionally, minimum and maximum values to which a threshold percentage can be set are developed. Without more, where high thresholds are employed, the signal level available for developing a drive for the LED array 44 or speaker 220 would be inadequate. A minimum threshold level is imposed to avoid sound outputs resulting from environmental noise. Such noise essentially is always at hand, being found to be stronger at some geographic areas than others. The adjusted count rate signal at line 264 is directed to a post threshold amplification network represented block 266. Network 266 is configured having a gain which corresponds with the threshold level value set at function 264 such that it carries out an amplification of the adjusted count rate signal at line 264 to provide an amplified count rate signal at line 268 which lies at levels within a predetermined output dynamic range. That dynamic range is established by the aural cuing and drive demands of the LED array or bar graph 44. In this regard, line 268 is tapped at line 270 and the signal thereat is directed to a bar graph driver function represented at block 272. Driver 272 then drives the array 44 as represented at line 274. Line 268 also is seen to be directed to a variable pitch generator represented at block 276. Generator 276 functions to produce a drive signal at line 278 which is directed to line 250 so as to produce a speaker drive output.

That output will be at a pitch corresponding with the drive signal asserted thereat and which lies between a zero pitch level and a maximum pitch level corresponding to the noted dynamic range which is maintained. Because, for the present embodiment, the microprocessor driven aural feedback from operation of the switches 226 is not present, an additional beep generator is provided as represented at block 280 which functions to generate a beep via line 250 at such time as any one of the switches 226 are actuated by the operator. Line 250 is reproduced from FIG. 4B as well as the designation for switch 208, line 206 and line 210. A more detailed description of the system 240 is provided in co-pending application for U.S. Pat. Ser. No. 08/944,078, filed Oct. 4, 1997, now U.S. Pat. No. 5,928,150, issued Jul. 27, 1999 entitled "System for Locating and Detecting a Source of Photon Emissions" by Call, assigned in common herewith.

Inasmuch as the relatively low gamma energy employed with the locator of the RIGS procedure is systemically injected, the type of signal which is removed by the energy window network 170 is a background radiation emanating from a systemic distribution of such radiation within the patients body. By contrast, the injection of substantially higher gamma energy fluid for the purpose of sentinel lymph node detection involves a non-systemic approach. In this regard, the radiopharmaceutical is injected at the site of a lesion and the probe 14 is used to track the lymph duct which tends to concentrate at one or more sentinel nodes.

Figure 6:
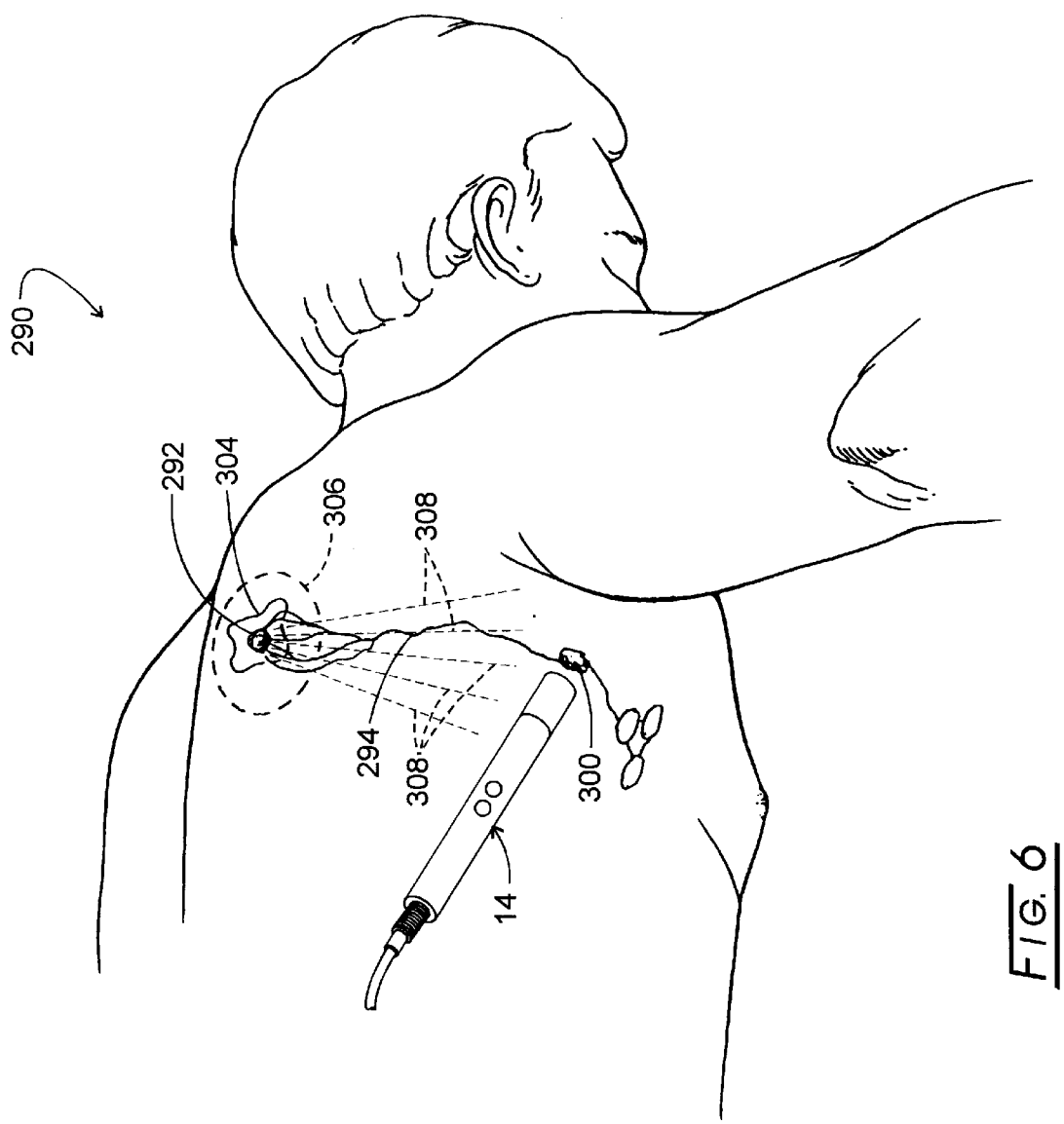
FIG. 6 is a view of the upper torso from the posterior aspect showing a cutaneous melanoma with lymph ducting to a sentinel mode.

Referring to FIG. 6, an illustration of the upper back of a patient is shown in general at 290 in conjunction with a cutaneous melanoma or lesion 292. The figure illustrates a lymph duct associated with lesion 292 as at 294 extending to a sentinel node as at 300. Lesion 292 is visually identified by the practitioner, whereupon a radiopharmaceutical is injected in quadrature to result in a lobed boundary of relatively high count rate activity represented at 304. Following an interval of time permitting migration of the radio-pharmaceutical along the duct 294, an initial scan along a locus, for example, a circular locus surrounding and spaced from the site of the neoplastic tissue 292 as well as boundary 304 is carried out as represented by the dashed circle 306. This procedure will locate the appropriate lymph duct 294 carrying radiopharmaceutical. A sequence of traverses are carried out, for example, transversely to the duct 294 until a higher level of radiation is detected as the probe 14 is positioned over sentinel node 300. It is dissected and submitted for evaluation with respect to potential metastasis. For this utilization of the probe 14, the type of background encountered will be Compton scattering of radiation from the lobe region 304. It is this form of background radiation that is to be windowed out for this mode of operation of probe 14. The Compton scattered radiation is represented in the figure by dashed lines certain of which are identified at 308.

Semiconductor crystals as at 88 employed with the instant invention, by virtue of the use to which they are put, are those which are described as being operable at room temperatures. The compound semiconductor which is cadmium telluride based and, more particularly is formed of cadmium zinc telluride is the preferred device for probes at 14. Ionizing radiation interactions in these semiconductors excite bound electrons that create a high density of electron-hole pairs. It is the subsequent motion of these electrons and holes under the influence of an electric field that is the origin of the basic electrical signal from a semiconductor detector. For every electron excited into the conduction band, a hole remains in the valance band. It is the motion of both charge carriers that contributes to the observed output signal. Four distinguishable conditions may exist in a semiconductor radiation detector. They are:

1) Complete carrier extraction in which both electrons and holes are removed from the device depletion region with high efficiency.
2) Short-term trapping of the carriers in which carriers are briefly trapped, but undergo detrapping and are extracted from the detector within the pulse processing shaping time of the device.
3) Long term trapping in which carriers undergo trapping and are not detrapped or extracted within the shaping time.
4) Partial recombination of the carriers in which carriers are lost due to recombination effects. If it is assume that one carrier type (e.g., electrons) follows condition 1 and the other (holes) follows condition 2 (short term trapping and detrapping), the pulse shape becomes a function of the interaction position in the detector. If the interaction occurs at the negative electrode, the charge contribution from hole movement is zero and the pulse shape becomes a function of the electron movement entirely. However, at other positions in the detector where hole movement now becomes important, the pulse changes in accordance with the charge contribution of the holes. If the hole extraction time is long compared to the hole lifetime, the holes may undergo multiple trapping and detrapping. See generally: "Semiconductors for Room-Temperature Radiation Detector Applications," Materials Research Society Symposium Proceedings, Vol. 302, p. 9.

Figure 7:
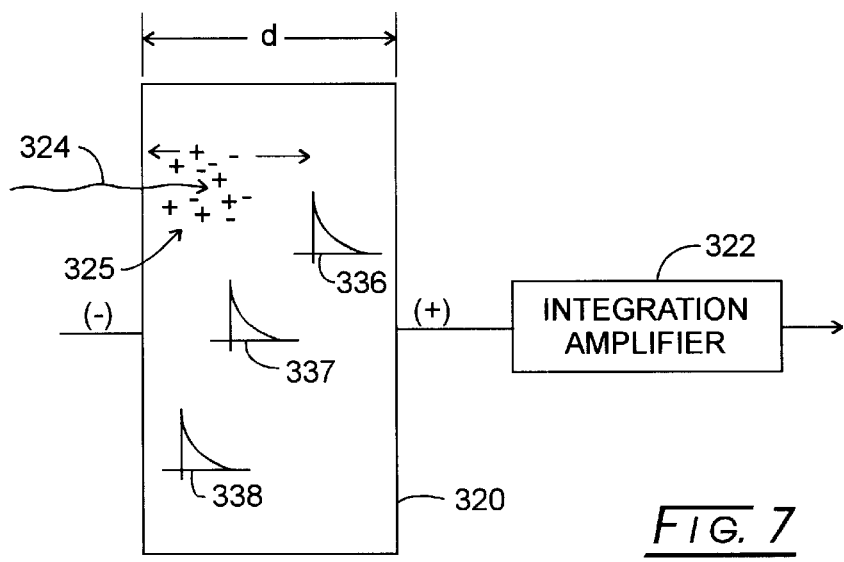
FIG. 7 is a schematic representation of a semiconductor crystal and associated integrating amplification stage employed with the invention.
Figure 8:
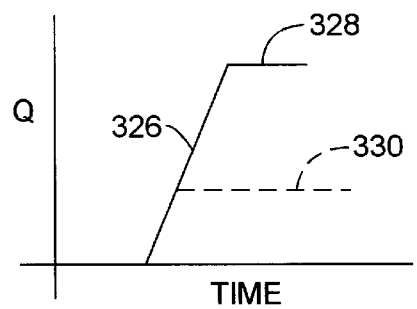
FIG. 8 is a stylized graph plotting charge versus time.

A carrier deriving arrangement is schematically portrayed in FIG. 7. Looking to that figure, a cadmium telluride crystal is schematically portrayed at 320. An electrical field or bias is applied to the crystal 320, the right side of the crystal being shown held at a positive field state and the left side being at a ground field state. The positive side of crystal 320 is electrically coupled with an integrating amplifier as represented at block 322. In somewhat ideal operation, when a gamma ray as represented at 324 interacts within the volume of crystal 320, an electron will be excited and the excitation may be a photoelectric transition (all the energy of the gamma ray is imparted to the electron). Alternately, the gaima ray may bounce off an electron to evoke Compton scattering with reduced energy and change in wavelength. The engaged electron moves with the residual energy of the engagement. In either case, the electron is given a relatively enormous amount of energy, for example, typically in values of thousands of electron volts, whereas normally, the electron will have an energy on the order of a fraction to a few electron volts. The process where collision with other electrons occurs, giving up part of its energy until a large number of electrons share all of this energy is sometimes referred to as a "cloud". Such a cloud is represented in FIG. 7 in general at 325. As noted above, for each of these electrons there is a hole to provide a carrier pair. Because of the electric field, electrons move toward the positively biased face of the crystal and holes migrate toward the grounded surface of crystal 320. Inasmuch as an integrating amplifier as at 322 is at the output of the system, there is evoked an integration of the current carried by these moving charges. Looking to FIG. 8, the result is a voltage or charge, Q, which, as represented at curve 326, elevates under ideal conditions to a maximum value 328 when all of the charge is collected. In general, the change in voltage on the output of the integrator 322 is proportional to the energy of the incoming gamma ray, or at least is proportional to the energy given to the electrons. Additionally the ideal performance is stylistically represented in FIG. 9, where a multi-channel analyzer (MCA) output plotting counts verses energy would trace a highly desired spectra distribution of counts with essentially no trapping and corresponding amplitudes as represented at curve 333. Such ideal performance, however, is seldomly if ever achieved with semiconductors. In this regard, the electrons and holes may be trapped with impurity centers within the crystal. The crystals always will have small disruptions of the lattice where an atom is missing or an extra atom or an impurity atom is present. Those discontinuities can trap electrons and holes. When an electron starts out, for example, following a collision with gamma ray 324 (FIG. 7) it will move with a velocity that is determined by the electric field. This velocity may be expressed as follows:

$$\bar{v} = m\bar{E} \qquad (1)$$

where $\bar{v}$ is velocity, m is mobility and $\bar{E}$ is electric field. The electric field $\bar{E}$, may be expressed as follows:

$$E = \frac{v}{d} \qquad (2)$$

where v is velocity and, d, is the thickness distance of the crystal, the latter being as represented in conjunction with FIG. 7. Thus all electrons move at the same velocity and velocity times charge then provides a value for current. Under ideal conditions, the "transit time" of the carriers migrating to the crystal faces will be quite short. In this regard transit time will be short as compared to a migration interval or time which will elicit trapping, i.e. a "trapping time." Where the carriers are trapped, for any given electron, current is terminated and a smaller charge is realized. The result of such trapping is an erratic curve and a lower maximum value as seen at 330 in FIG. 8. If the trapping is excessive, most of the derived counts will be at low energy values and the output under typically higher bias voltage levels is no longer available as a device for measuring energy. Such a result is represented at curve 332 in the simulated MCA plot of FIG. 9.

Now considering the preferred detector, cadmium zinc telluride the velocity of holes and electrons for any given carrier evoked in this semiconductor are not the same. In this regard, the velocity of the electrons for this crystal is about twelve times that of holes. Thus, a long dwell time is present for hole motion and most of them become trapped. Additionally, some of the electrons are trapped and the result is an unusable count/energy distribution again represented by the dashed curve 332 shown in stylized fashion in FIG. 9.

As noted above, a mode of operation of cadmium telluride crystals essentially overcoming the trapping difficulties is developed through the use of an extremely pure crystal structure with very few impurities. For example, the impurities should occur in less than parts per billion. Additionally, where residual trapping centers are present, investigators will use a very high bias voltage, for example, in the 500 to 700 volt range to enhance transit time. This generally will produce a sharp peak in an MCA curve as at 333 shown at FIG. 9. This high purity and high bias voltage approach is essentially a standard mode for operating these detectors. Such costly detectors are typically used in spectroscopy research.

For applications including those in the medical field, high purity cadmium telluride detectors are prohibitively expensive. In this regard, the compound semiconductors must have equal numbers of atoms of cadmium and tellurium atoms. A slight unbalance will result in excessive traps. Where the detectors are formed of cadmium zinc telluride, then the number of cadmium and zinc atoms should equal the number of tellurium atoms. Unfortunately, cadmium is very volatile and the crystals are drawn at high temperatures. Thus, the cadmium tends to evaporate and the problematic formation to achieve highly pure crystals is an expensive process.

Figure 9:
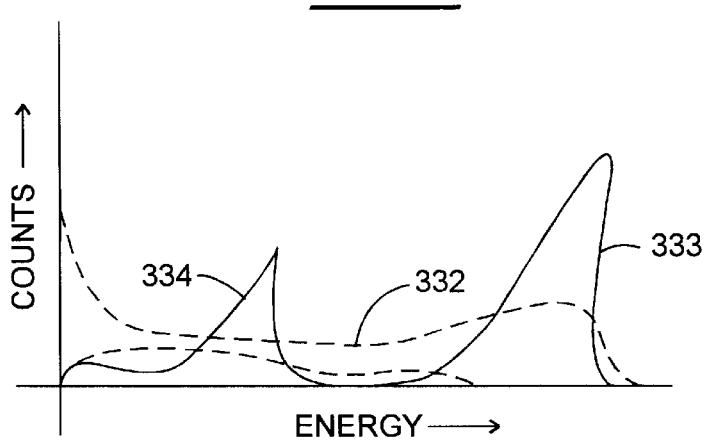
FIG. 9 is a stylized multi-channel analyzer plot showing counts versus gamma energy.

Returning to FIG. 7, where the cadmium telluride crystals are used for the RIGS procedure, with relatively thin (2 mm) CdZnTe crystals, excellent performance of the crystals is achieved. For the procedure, a low gamma energy radionuclide, $^{125}$I is used (27 to 35.2 Kev). Accordingly, as a gamma ray, for example, such as at 324 contacts the forward face of crystal 320, the holes are captured immediately at the left or forward face boundary and the electrons all travel the same distance within the detector volume. Thus, a high quality crystal structure is not required and a high voltage bias is not used. Plots as at 333 in FIG. 9 are realized.

The difficulties of operating the cadmium telluride crystal having a thickness of 2 mm or greater and performing with a relatively higher bias voltage level resides in the location of the interaction with an electron within the crystal volume and varying degrees of trapping. This particularly is the case with respect to high gamma energy sources, for example, $^{99m}$Tc. The variation in interaction and variations in trapping results in an MCA plot having a very flat or broad photopeak and a wide energy distribution resulting in poor probe performance for this mode of operation. Plots as at 332 in FIG. 9 may result.

In accordance with the present invention, however, the crystal 320 is made relatively thicker, i.e., 4 mm and relatively lower bias voltage is employed. This creates a mode of operation which may be deemed a "trapping dependent operational mode". Returning to FIG. 7, with a relatively low bias and a thicker crystal, gamma ray electron interaction will occur throughout the volume of the crystal, for illustrative example, at locations represented by small graphs 336–338. With this arrangement, the number of electrons reaching the right hand or positive side of crystal 320 approaches zero due to trapping. There now occurs a dominance of trapping time over carrier transit time. This gradual trapping phenomenon is represented by the exponential curves also shown at graphs 336–338. Even though the electrons do not reach the positive face of the crystal 320 they do move and cause a current which is integrated to provide a charge. For example, the interaction at 336 occurs near the right hand face of crystal 320 and that at 337 occurs toward the middle. However, both make the same contribution to charge. This also is the case for an interaction occurring at 338. The charge will be smaller because electrons have been lost, and the maximum value described at 328 in FIG. 8 for charge will be lowered somewhat. The resulting energy and count distribution on an MCA plot will see a desirably sharp curve as at 333 occur but the curve will move to the left toward a lower energy value as at 334. Thus configured, the crystal is seen to perform adequately with both low gamma energy radionuclides as well as higher ones, for example, at 140 Kev energy levels.

With the arrangement shown, expensive, very highly pure cadmium zinc telluride crystals are not required and very high bias voltages are not required. The latter high voltages are undesirable inasmuch as passage of high voltage through cable 22 is not desirable; connectors are more expensive; and the signal treatment circuit becomes more expensive to implement.

Figure 10:
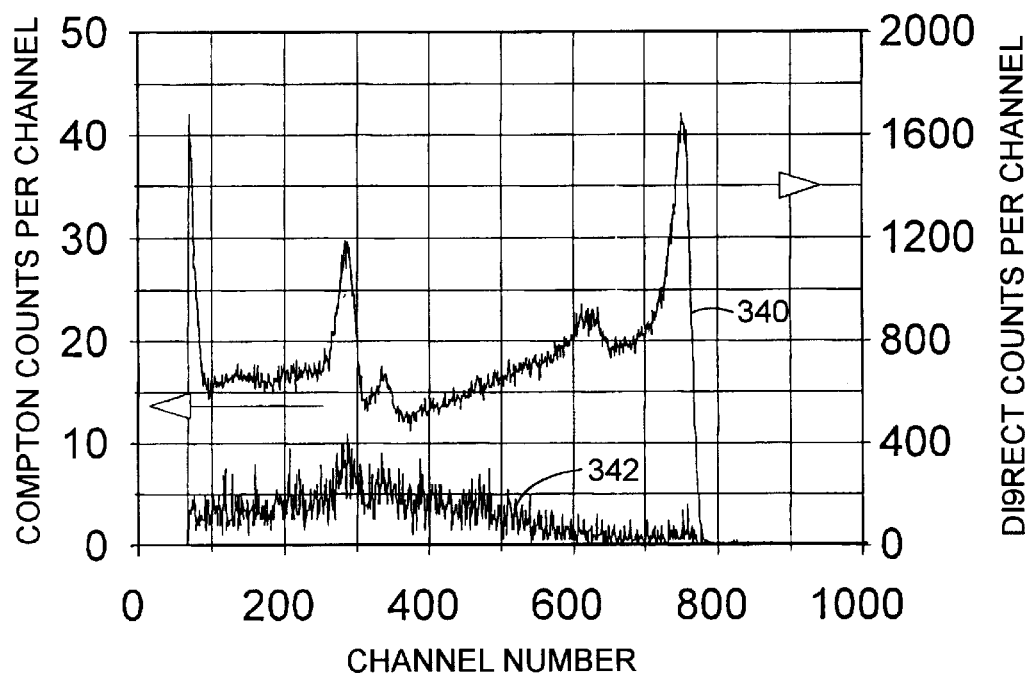
FIG. 10 is a multi-channel analyzer plot showing direct counts per channel as well as Compton counts per channel.

Referring to FIG. 10, an MCA plot is depicted which was developed utilizing a hand-held probe with a cadmium zinc telluride crystal having a thickness, d, of 2 mm and operated under a bias of 180 volts. The source under detection was $^{99m}$Tc (140 Kev). Compton scattering represented as counts per channel are separately plotted at the bottom of the graph and are seen to extend substantially into higher energy channels. Poor performance is noted, the semiconductor crystal not operating in a trapping dependent operational mode. Windowing for such crystal operation would be located at a channel position of about 650 with a dependent loss of counts.

Figure 11:
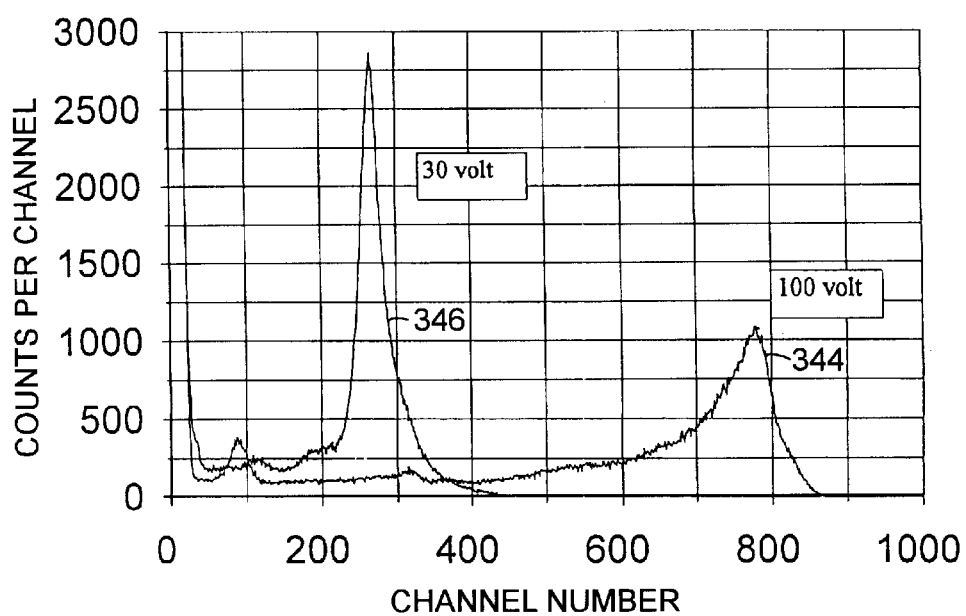
FIG. 11 is a multi-channel analyzer plot showing counts per channel versus channel number for two bias voltages.

Looking to FIG. 11, two MCA plots are provided for a hand-held probe having a cadmium zinc telluride crystal with a thickness, d, of 4 mm. The source detected with this experiment was $^{99m}$Tc. Plot 344 shows performance of the probe with a 100 volt bias. Note that the photopeak is just over 1000 counts. Plot 344 has a shape such that, where the counts or pulses that are within 20% of the photopeaks are elected for counting, 53% of the total counts will be evaluated by the system. However, as represented at plot 346, when a much lower, 30 volt bias is applied to the semiconductor crystal, a desirable very sharp photppeak is evoked and counts or pulses within 20% of the photopeak of the plot will provide a system count output wherein 78% of the counts are collected. Note, however, that the photopeak at plot 346 has moved toward a lower energy channel.

Figure 12:
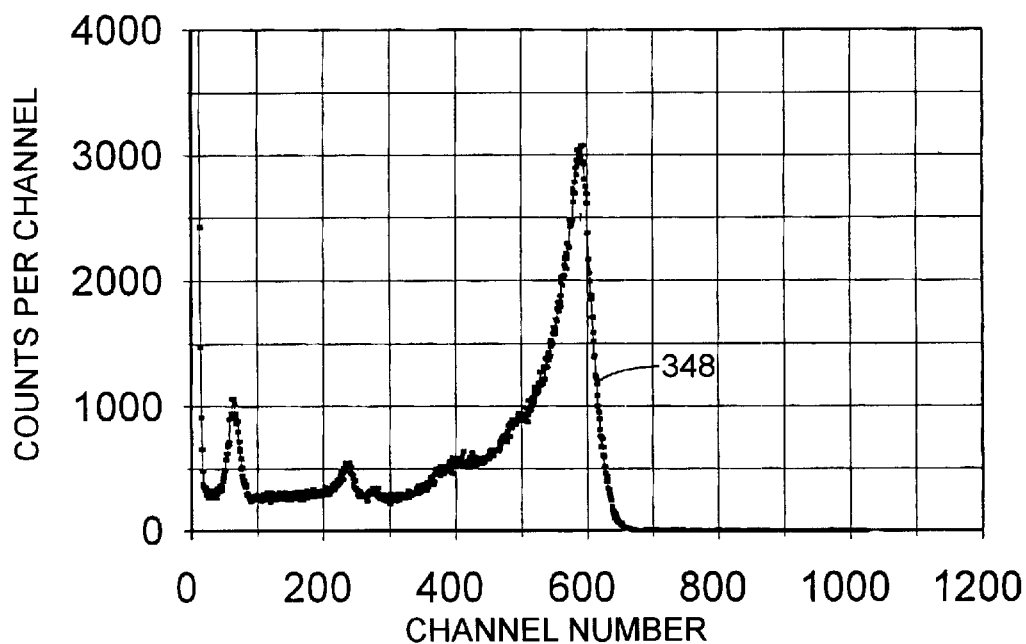
FIG. 12 is a multi-channel analyzer plot showing counts per channel versus channel number.

Referring to FIG. 12, an MCA plot is provided showing the performances of a hand-held probe having a cadmium zinc telluride detector crystal of 4 mm thickness which responds to $^{99m}$Tc under a bias of 100 volts. The plot at 348 is normalized to 50 micro Ci and shows a desirably sharp photopeak in the vicinity of channel 600. Compton scattering is readily windowed out with such performance. The crystal had a thickness , d, of 4 mm.

Figure 13:
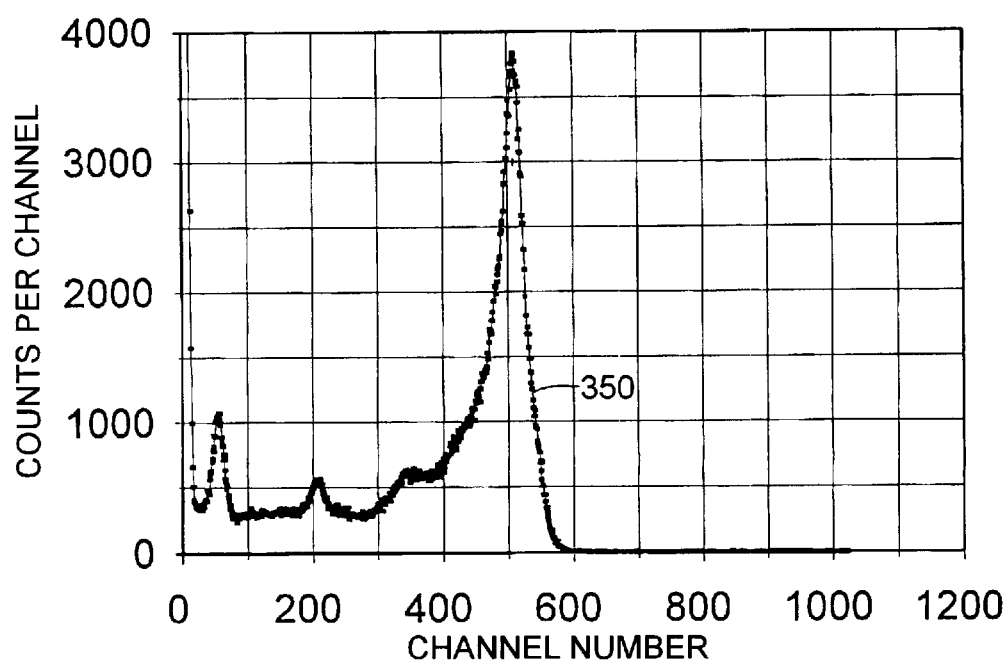
FIG. 13 is a multi-channel analyzer plot showing counts per channel versus channel number.

Referring to FIG. 13, the same hand-held probe as utilized in connection with FIG. 12 is shown tested with the same source but at a bias of 80 volts. The plot is normalized to 250 micro Ci Note the very sharp photopeak in plot 350 and that the photopeak has moved toward a lower energy channel position as compared to plot 348.

Figure 14:
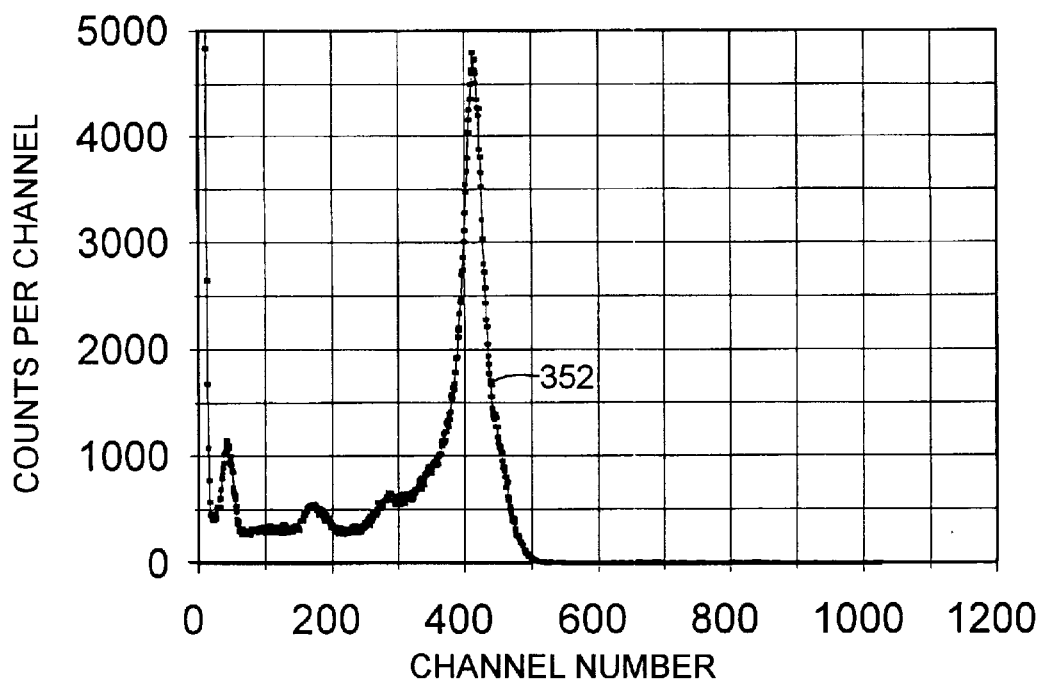
FIG. 14 is a multi-channel analyzer plot showing counts per channel versus channel number.
Figure 15:
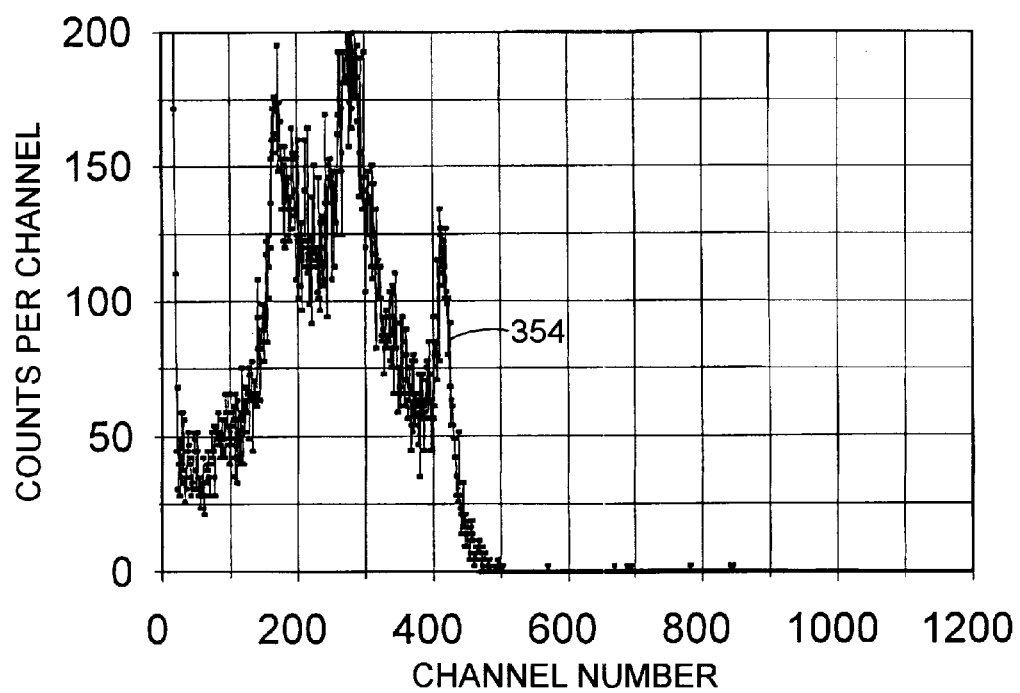
FIG. 15 is a multi-channel analyzer plot showing counts per channel versus channel number for Compton scattering.

Referring to FIG. 14, another MCA plot is provided at plot 352, plot 352 was derived using tie same hand-held probe as described in connection with FIG. 12 in conjunction with $^{99m}$Tc . The plot is normalized to 50 micro Ci and shows a sharp photopeak which has moved, as before, toward a lower energy channel position as compared with plot 352. Looking additionally to FIG. 15, Compton scattering was separately plotted at 354 for the test associated with FIG. 14. Plot 354 is at a greatly enlarged scale and shows very low counts per channel at the low energy 200 to 300 channel positions. This Compton scattering is readily windowed out. Experience and testing has shown that the 60 volt bias in conjunction with a cadmium telluride crystal having a thickness, d, of 4 mm is an optimum architecture for the alternate use with low energy $^{125}$I as used in the RIGS system as well as with the higher energy $^{99m}$Tc employed in locating and removing sentinel lymph nodes.

Figure 16:
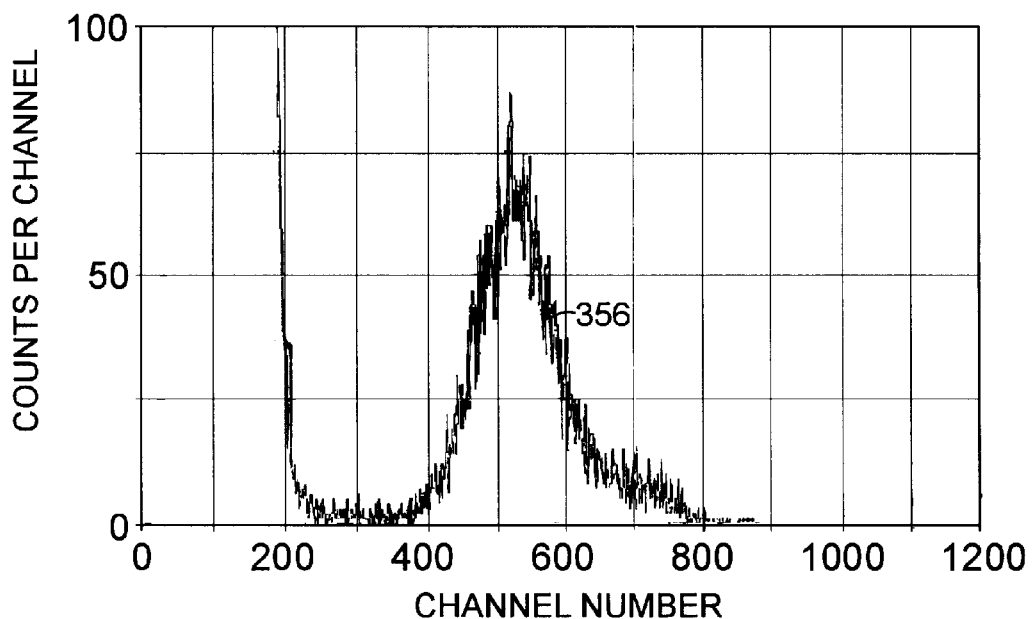
FIG. 16 is a multi-channel analyzer plot showing counts per channel versus channel number.

Referring to FIG. 16, an MCA plot 356 is shown. Plot 356 was developed using a $^{129}$I (less than 40 Kev) source (low energy) with a hand-held probe having a cadmium zinc telluride crystal of 12 mm diameter and 4 mm thickness. While the counts per channel for this low energy radionuclide are, as expected, low, the shape of plot 356 shows a sharpness or acceptable performance.

Figure 17:
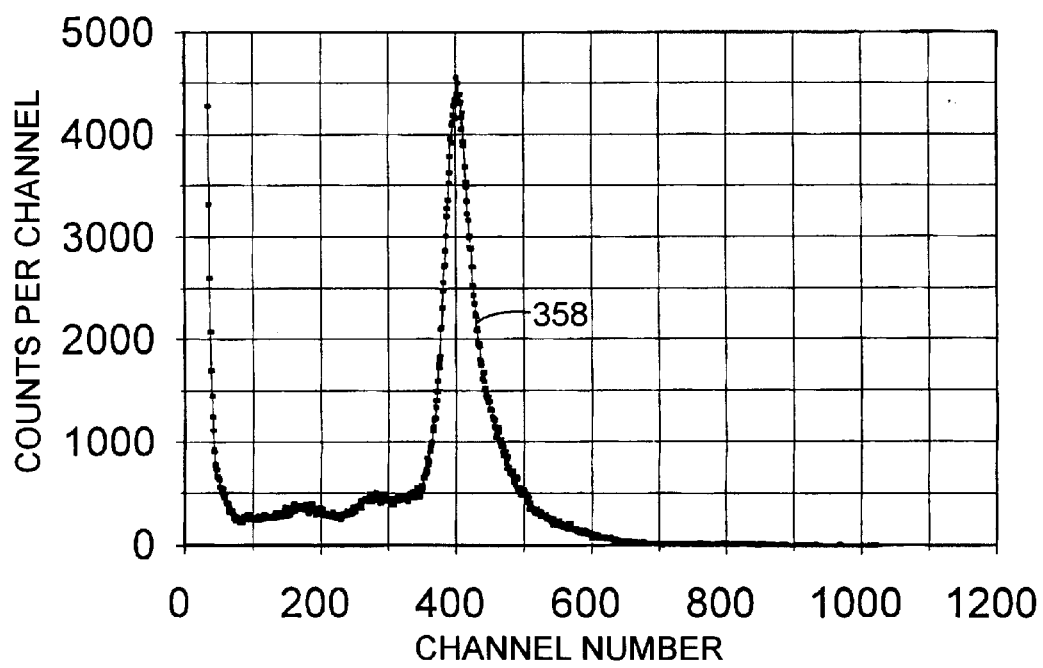
FIG. 17 is a multi-channel analyzer plot showing counts per channel versus channel number.

Referring to FIG. 17, the same probe utilized in the test carried out in conjunction with FIG. 12 was tested in conjunction with $^{99m}$Tc under a bias of 30 volts. Plot 358 is normalized to 50 micro Ci. Note the sharp photopeak.

Figure 18:
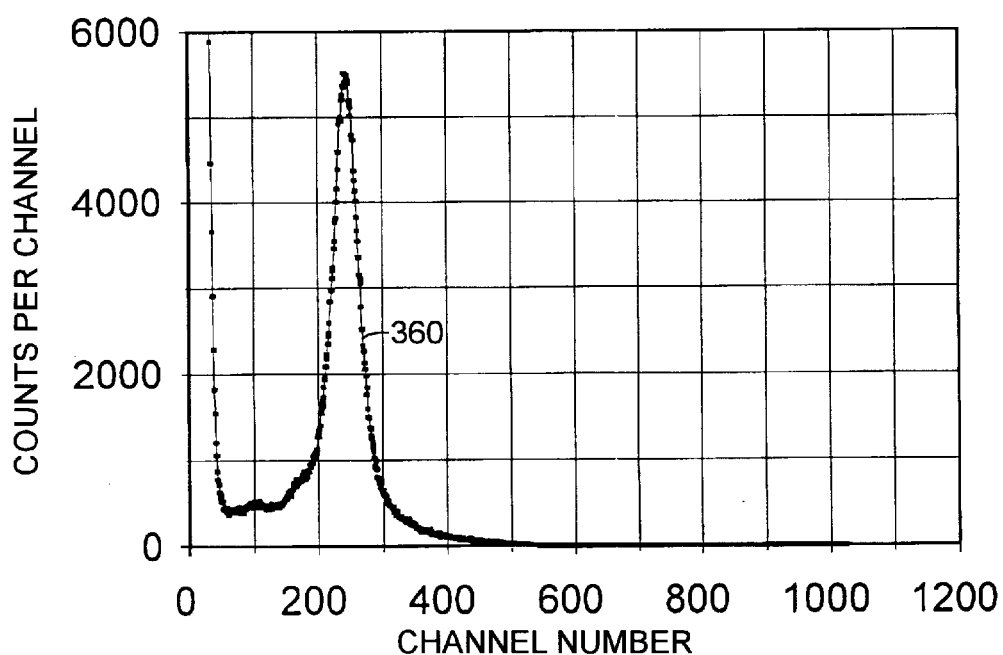
FIG. 18 is a multi-channel analyzer plot showing counts per channel versus channel number.

Referring to FIG. 18, the same probe is utilized in the test carried out in conjunction with FIG. 12 was employed with a test source of $^{99m}$Tc. The probe was operated at a 20 volt bias. Plot 360 is normalized to 50 micro Ci and again shows a sharp photopeak.

Figure 19:
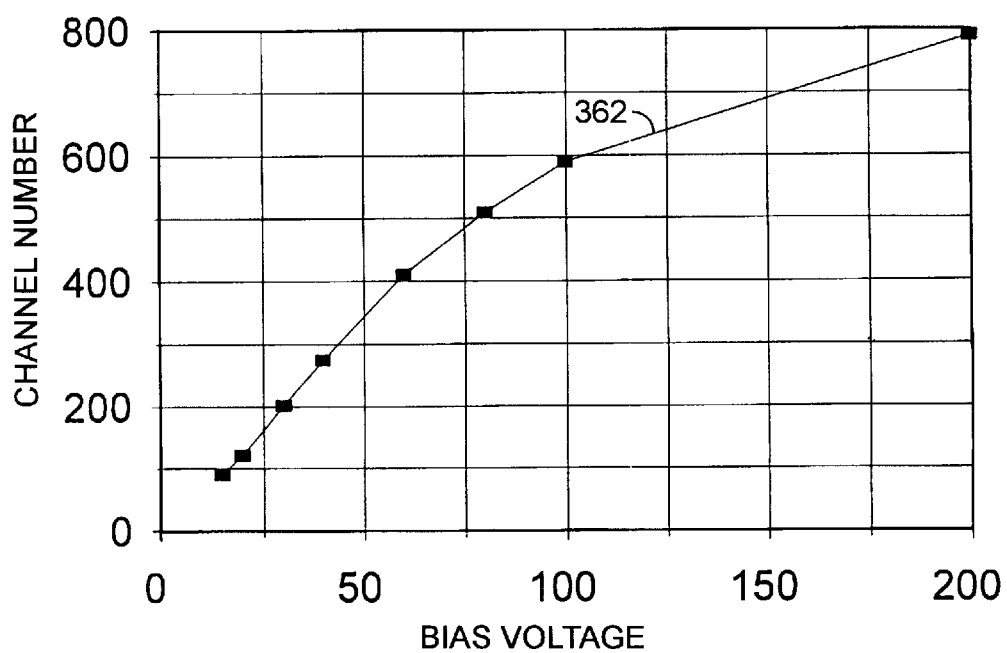
FIG. 19 is a graph comparing photopeak positions with respect to channel number and bias voltage.

Referring to FIG. 19, a curve 362 is provided which was generated utilizing the same hand-held probe described in conjunction with FIG. 12. In the figure, the photopeak positions developed in testing are plotted with respect to applied bias voltage and to channel number. Note that the curve 362 diminishes in channel number location as bias voltage is lowered. While the photopeaks appear desirably sharp, for example below a 60 volt bias, they are located in close proximity to noise. As a result, it is difficult to set a window to achieve desired performance. In general, the bias should be within a range of about 100 volts to 60 volts. A bias value of 60 volts, as noted above, has been found to be an optimum selection of bias voltage for the alternate use of the detectors with low energy $^{125}$I and higher energy $^{99m}$Tc.

Figure 20:
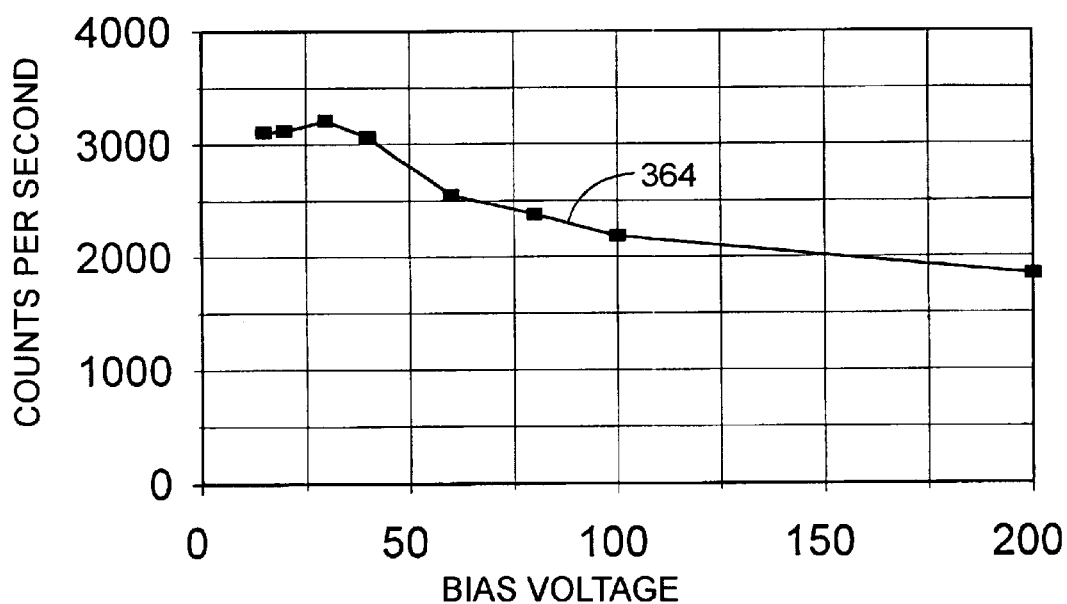
FIG. 20 is a graph relating photopeak counts per second versus bias voltage.

Looking to FIG. 20, a curve 364 is provided which relates the bias voltage for the probe of FIG. 12 with counts per second in the photopeak. As before, the curve 364 was derived utilizing $^{99m}$Tc as the radiation source and the photopeak plots were nonnalized to 50 micro Ci.

Curve 364 suggests additionally that the area under the MCA curve (total counts) in substantially independent of the level of bias voltage.

Since certain changes may be made to the above described system, method and apparatus without departing from the scope of the invention herein involved, it is intended that all matter contained in the description thereof and shown in the accompanying drawings shall be interpreted as illustrative and not in a limiting sense.

What is claimed is:

1. Apparatus for detecting and locating a source of radiation having a given gamma energy level, comprising:

a housing having a forward portion extending to a radiation transmissive window positionable in the vicinity of said source;

a cadmium telluride semiconductor crystal detector mounted within said housing, having a forward face adjacent said window and extending a thickness distance, d, to a rearward face, said crystal detector being operative under applied bias, and said thickness distance, d, being effective to derive a trapping-dependent operational mode wherein a trapping of substantially all gamma radiation derived carriers is effected to derive a count related charge output;

a signal treatment network responsive to said count related charge output for carrying out an energy level based validation thereof and deriving count signals;

a bias generating circuit for deriving said bias input at a voltage level effective to derive said trapping-dependent operational mode wherein said count related charge output is at a gamma energy level exhibiting a photopeak effective to carry out said validation; and perceptible indicator means for providing a perceptible output corresponding with said count signals.

2. The apparatus of claim 1 in which:

said thickness distance, d, is about 4 millimeters.

3. The apparatus of claim 1 in which said bias generating circuit derives said bias input at a voltage level of between about 60 and 100 volts.

4. The apparatus of claim 1 in which:

said thickness distance, d, in about 4 millimeters; and said bias generating circuit derives said bias input at a voltage level of between about 60 and 100 volts.

5. The method of operating a crystal detector for detecting and locating a source of radiation having a given energy level, comprising the steps of:

providing a hand manipulable housing having a forward portion extending to a radiation transmissive window;

providing a room temperature operable telluride crystal detector within said housing, said crystal detector having a forward face adjacent said window and extending a thickness distance, d, to a rearward face, said thickness distance, d, being effective for the operation of said crystal detector in a trapping-dependent operational mode wherein a trapping of substantially all carriers formed within the volume of said detector is effected to derive a count related charge output;

applying a bias across said crystal detector at a voltage level effective to derive said trapping-dependent operational mode wherein said current related output is at an energy level and exhibits a photopeak effective for carrying out a validation windowing of noise; and windowing out said noise at an energy level below said photopeak.

6. The method of claim 5 in which said crystal detector is cadmium telluride having a said thickness distance, d, of about 4 mm.

7. The method of claim 5 in which said crystal detector is cadmium telluride and said bias is applied at a voltage within a range from about 60 volts to 100 volts.

8. The method of claim 7 in which said cadmium telluride crystal detector thickness distance, d, is about 4 mm.

9. The method of claim 5 in which said crystal detector is cadmium telluride and said bias is applied at 60 volts.

10. The method of claim 9 in which said cadmium telluride crystal detector thickness distance, d, is about 4 mm.

11. Apparatus for detecting and locating a first source of radiation having a first energy level and, alternately, a second source of radiation having a second energy level greater than said first energy level, said first and second sources being within regions of interest, comprising:

a probe movable within said regions of interest, including;

a housing having a forward portion extending to a radiation transmissive window positionable in the vicinity of said source;

a room temperature operable semiconductor crystal detector within said housing having a forward face adjacent said window and extending a thickness distance, d, to a rearward face, said crystal detector being operative under a an applied bias, and said thickness distance, d, being effective to derive a trapping-dependent operational mode wherein a trapping of substantially all photon event derived carriers generated by radiation impinging upon said detector forward face from said first and second sources is effected to derive a count related charge output;

a biasing network electrically coupled across said forward and rearward faces of said detector and responsive to a bias input for applying said bias;

a control system including;

a signal treatment network responsive to said count related charge output for carrying out an energy level based validation thereof and deriving count signals;

a bias generating circuit for deriving said bias input at a voltage level effective to derive said trapping-dependent operational mode wherein said count related charge output is at an energy level exhibiting a photopeak effective to carry out said validation; and perceptible indicator means for providing a perceptible output corresponding with said count signals.

12. The apparatus of claim 11 in which:

said semiconductor crystal detector is a cadmium telluride crystal; and said thickness, d, is about four millimeters.

13. The apparatus of claim 11 in which said bias generating circuit derives said bias input at a voltage level of between about 60 and 100 volts.

14. The apparatus of claim 11 in which:

said semiconductor crystal detector is a cadmium telluride crystal; and said bias generating circuit derives said bias input at a voltage level of between about 60 and 100 volts.

15. The apparatus of claim 14 in which said thickness, d, is about four millimeters.

16. The apparatus of claim 11 in which:

said semiconductor crystal detector comprises a cadmium telluride crystal; and said bias generating circuit derives said bias input at a voltage level of about 60 volts.

17. A medical system for detecting and locating a systemically injected locator radiolabeled with a radionuclide exhibiting a gaima energy level of about 40 Kev, and for detecting a non-systemically injected radiopharmaceutical exhibiting a gamma energy level substantially higher than 40 Kev, comprising:

a probe including;

a housing having a forward portion extending to a radiation transmissive window;

a room temperature operable semiconductor crystal detector within said housing having a forward face adjacent said window and extending a thickness distance, d, to a rearward face, said thickness distance, d, being effective for the operation of said detector in a trapping-dependent operational mode wherein a trapping of substantially all carriers formed within the volume of said detector, from either said locator or said radiopharmaceutical, is effected to derive a count related charge output;

a biasing network electrically coupled with said forward and rearward face of said detector for applying an electric field generating bias input there across;

a control system, including;

a signal treatment network responsive to said count related charge output for carrying out an energy level based validation thereof and deriving count signals;

a bias generating circuit for deriving said bias input at a voltage level effective to derive said trapping-dependent operational mode wherein said count related charge output is at an energy level and exhibits a photopeak effective to carry out said validation; and perceptible indicator means for providing a perceptible output corresponding with said count signals.

18. The system of claim 17 in which:

said semiconductor crystal detector is a cadmium telluride crystal; and said thickness, d, is about four millimeters.

19. The system of claim 17 in which said bias generating current derives said bias input at a voltage level of between about 60 and 100 volts.

20. The system of claim 17 in which:

said semiconductor crystal detector is a cadmium telluride crystal; and said bias generating circuit derives said bias input at a voltage level of between about 60 and 100 volts.

21. The system of claim 20 in which said thickness, d, is about four millimeters.

22. The system of claim 21 in which said radiopharmaceutical exhibits a gamma energy level of about 140 Kev.

23. The system of claim 21 in which said bias generating circuit derives said bias input at a voltage level of about 60 volts.

24. The method for operating a cadmium telluride crystal detector for detecting and locating a systemically injected locator radiolabeled with a radionuclide exhibiting a gamma energy level of about 40 Kev, and for detecting a non-systemic radiopharmaceutical exhibiting a gamma energy level substantially higher than 40 Kev, comprising the steps of:

providing a hand manipulable housing having a forward portion extending to a radiation transmissive window;

providing a cadmium telluride crystal within said housing, said crystal detector having a forward face adjacent said window and extending a thickness distance, d, to a rearward face, said thickness distance, d, being effective for the operation of said crystal detector in a trapping-dependent operational mode wherein a trapping of substantially all carriers formed within the volume of said detector, from either said locator or said radiopharmaceutical, is effected to derive a count related charge output;

applying a bias across said crystal detector at a voltage level effective to derive said trapping-dependent operational mode wherein said count related output is at an energy level and exhibits a photopeak effective for carrying out a validation windowing of noise; and windowing out said noise at an energy level below said photopeak.

25. The method of claim 24 in which said cadmium telluride crystal detector thickness distance, d, is about 4 mm.

26. The method of claim 24 in which said bias is applied at a voltage within a range from about 60 volts to 100 volts.

27. The method of claim 26 in which said cadmium telluride crystal detector thickness distance, d, is about 4 mm.

28. The method of claim 24 in which said bias is applied at 60 volts.

29. The method of claim 28 in which said cadmium telluride crystal detector thickness distance, d, is about 4 mm.

* * * * *